(12) United States Patent
Heneveld

(10) Patent No.: US 11,452,519 B2
(45) Date of Patent: *Sep. 27, 2022

(54) APPARATUS AND METHOD FOR PASSING SUTURE THROUGH SOFT TISSUE

(71) Applicant: Passer Stitch, LLC, Whitmore, CA (US)

(72) Inventor: Scott Heneveld, Whitmore, CA (US)

(73) Assignee: Passer Stitch, LLC, Whitmore, CA (US)

( * ) Notice: Subject to any disclaimer, the term of this patent is extended or adjusted under 35 U.S.C. 154(b) by 322 days.

This patent is subject to a terminal disclaimer.

(21) Appl. No.: 16/944,948

(22) Filed: Jul. 31, 2020

(65) Prior Publication Data

US 2020/0360012 A1 Nov. 19, 2020

Related U.S. Application Data

(63) Continuation of application No. 16/268,215, filed on Feb. 5, 2019, now Pat. No. 10,765,422, and a continuation-in-part of application No. 15/450,206, filed on Mar. 6, 2017, now abandoned, and a continuation of application No. 14/120,243, filed on May 8, 2014, now Pat. No. 9,610,075, and a continuation of application No. PCT/US2012/027782, filed on Mar. 5, 2012.

(51) Int. Cl.
*A61B 17/04* (2006.01)
*A61B 17/00* (2006.01)
*A61B 17/06* (2006.01)

(52) U.S. Cl.
CPC ...... *A61B 17/0469* (2013.01); *A61B 17/0482* (2013.01); *A61B 17/0483* (2013.01); *A61B 17/06004* (2013.01); *A61B 17/06066* (2013.01); *A61B 2017/00367* (2013.01); *A61B 2017/00867* (2013.01); *A61B 2017/0472* (2013.01); *A61B 2017/061* (2013.01); *A61B 2017/0608* (2013.01); *A61B 2017/06042* (2013.01); *A61B 2017/06052* (2013.01); *A61B 2017/06095* (2013.01)

(58) Field of Classification Search
CPC ............ A61B 17/0469; A61B 17/0482; A61B 17/06066; A61B 17/06004; A61B 17/0483; A61B 2017/00367; A61B 2017/06052; A61B 2017/0409
See application file for complete search history.

(56) References Cited

U.S. PATENT DOCUMENTS

2008/0208221 A1* 8/2008 Murray .............. A61B 17/0625 606/145

* cited by examiner

*Primary Examiner* — Majid Jamialahmadi
(74) *Attorney, Agent, or Firm* — Francis Law Group

(57) ABSTRACT

A system for passing suture through biological tissue using a cannula, introducer or other minimally invasive means, to approximate, ligate, fixate and/or close biological tissue. The system includes a hand grip in operative communication with an elongated tubular member having a jaw mechanism disposed on the tubular member distal end. The elongated tubular member housing a deformable tubular needle therein having a curvilinear portion and an internal lumen.

8 Claims, 17 Drawing Sheets

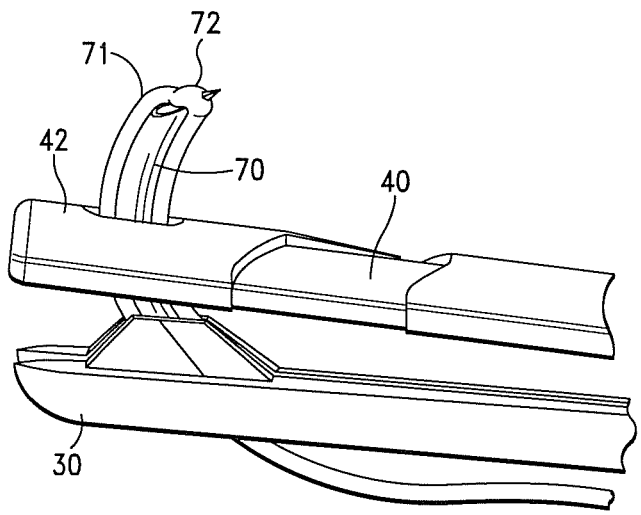
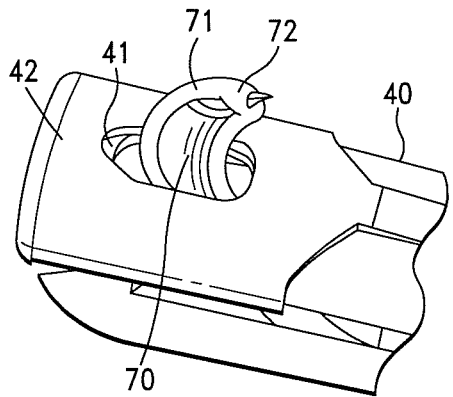
FIG. 6A        FIG. 6B
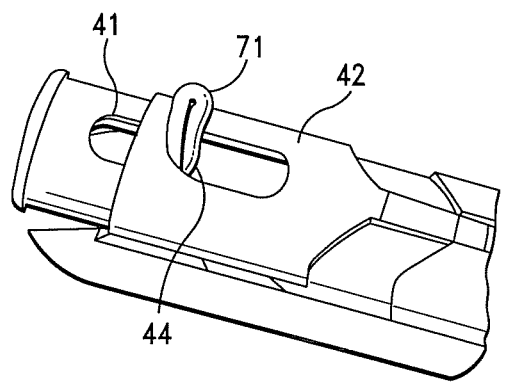
FIG. 6C
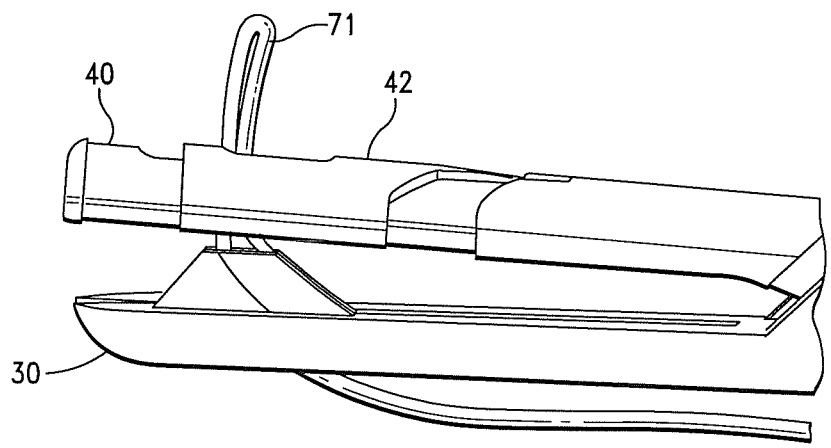
FIG. 6D

APPARATUS AND METHOD FOR PASSING SUTURE THROUGH SOFT TISSUE

CROSS REFERENCE TO RELATED APPLICATIONS

This application is a continuation of U.S. application Ser. No. 16/268,215, filed on Feb. 5, 2019, which is a continuation-in-part of U.S. application Ser. No. 15/450,206, filed on Mar. 6, 2017, now abandoned, which is a continuation of U.S. application Ser. No. 14/120,243, filed on May 8, 2014, now U.S. Pat. No. 9,610,075, which is a continuation of PCT Application No. PCT/US2012/027782, filed on Mar. 5, 2012, which claims priority to Provisional Application No. 61/464,578, filed on Mar. 7, 2011.

FIELD OF THE INVENTION

The present invention relates to system, methods, and apparatus for enhancing the advancement and retention of suture through tissue.

BACKGROUND OF THE INVENTION

Suturing apparatuses in the past have had an elongate shaft and a low profile distal clamping mechanism to facilitate their use through cannulas in less invasive surgery. These devices have typically included opposing jaws which clamp onto the tissue to be sutured. The end segment of the suture is pre-positioned and secured at the distal end of one jaw member. Beyond the clamping motion, the mechanism for passing a suture between the jaws and through the tissue incorporates a bendable flat needle. The bendable needle advances distally within the jaw member, bringing it in contact with a segment of the suture. The needle has a notch which engages and secures the suture to carry it forward.

This distal advancement of the bendable needle also results in the leading end of the needle to approach and engage a ramp in the jaw member, deflecting the bendable needle in a direction toward the opposing jaw. The bending of the needle requires a high force and results in excess strain on the notched needle component. Fracture and failure of the bendable needle is a concern.

Additionally, capturing suture reliably after being passed through the tissue is also a feature not currently offered by the existing technologies. The ability to throw a horizontal mattress stitch with the desired stitch width without having to remove and reload the instrument is currently an unmet need. Another area of improvement is the need to clamp onto thick tissue and reliably pass suture.

Further, extension of the needle beyond the opposing jaw member and potentially puncturing tissue or bone is also a safety concern with existing technologies. This limits the versatility of existing technologies to create desired stitch patterns, such as the modified Mason-Allen stitch.

It is thus desirable to provide improved systems and methods for passing suture through biological tissue that substantially reduces or eliminates the disadvantages and drawbacks associated with conventional, known systems and methods for the advancement and retention of suture through tissue.

It is therefore an object of the present invention to provide systems and methods for passing suture through biological tissue that shields local biological tissue and bone from damage.

It is another object of the invention provide systems and methods for passing suture through biological tissue that allows a needle and/or suture to be driven into and through body tissue in an antegrade and retrograde direction during endoscopic procedures.

SUMMARY OF THE INVENTION

The present invention is directed to systems and methods for passing suture through biological tissue using a cannula, introducer or other minimally invasive means, to approximate, ligate, fixate and/or close biological tissue.

In a preferred embodiment, the suture passing device comprises a hand grip in operative communication with an elongated tubular member comprising an internal lumen and a jaw mechanism disposed on the elongated tubular member distal end.

In a preferred embodiment, the jaw mechanism comprises top and bottom members that are movable with respect to each other.

In some embodiments, the jaw mechanism bottom member comprises a first guide channel and the jaw mechanism top member comprises a second guide channel.

In some embodiments, the jaw mechanism top member comprises a pawl that is configured to provide a closure force that enables the pawl to capture at least a portion of suture between the pawl distal tip and the luminal wall of the top member guide channel.

In a preferred embodiment, the elongated tubular member comprises an internal lumen having a flexible tubular needle housed therein that is configured to carry a suture.

In a preferred embodiment, the suture passing device comprises a needle assembly that is configured to position a suture into and, optionally, through a tissue section.

In some embodiments, the needle assembly comprises at least one tubular needle having a tissue piercing distal end and a curvilinear portion. In a preferred embodiment, the tubular needle curvilinear portion is elastically deformable when in a constrained state and, upon release to an unconstrained state, reassumes the previous curvilinear shape.

In some embodiments, the tubular needle distal tip is configured to pierce and engage at least a portion of suture.

In a preferred embodiment, the tubular needle comprises an internal lumen that is configured to receive and contain a cleat member. In some embodiments, the cleat member partially extends from the tubular needle internal lumen and is configured to pierce and engage at least a portion of suture to prevent the suture from sliding down the tubular needle.

In some embodiments, the tubular needle comprises a hollow and rigid needle. In some embodiments, the tubular needle comprises a geometry where the area moment of inertia about the neutral bending axis is in the range of $23.0 \times 10^{-9}$–$300.0 \times 10^{-9}$ inches to the $4^{th}$ power, more preferably, the tubular needle comprises a geometry where the area moment of inertia about the neutral bending axis in the range of $25.0 \times 10^{-9}$–$75.0 \times 10^{-9}$ inches to the $4^{th}$ power, which allows the tubular needle to be driven into biological tissue with minimal deflection or skiving.

In some embodiments, the tubular needle is adapted to deform into a constrained state when the curvilinear portion of the tubular needle is advanced through the elongated tubular member internal lumen and into through the first guide channel of the jaw mechanism bottom member.

In some embodiments, the curvilinear portion of the tubular needle is adapted to reassume a curvilinear shape upon further advancement out of the first guide channel and into and through the second guide channel of the jaw mechanism top member.

In some embodiments, the jaw mechanism top member comprises a suture retriever component (or needle shield) that is configured to receive the tubular needle distal end without damaging the tubular needle distal end.

In a preferred embodiment, the needle shield comprises a deflecting trap-door mechanism that is configured to prevent the tubular needle distal end from proceeding beyond the top member and damaging extraneous biological tissue and bone.

In a preferred embodiment, the needle shield is configured to deflect and flex when the tubular needle distal end is slidably translated into the needle shield.

In some embodiments, the needle shield is configured to provide a closure force that enables the needle shield to capture at least a portion of suture.

In a preferred embodiment, the needle shield of the jaw mechanism top member enables antegrade and retrograde passing of suture during an endoscopic procedure, which allows an operator to generate a wide variety of stitch patterns including, without limitation, a modified Mason-Allen pattern.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIG. 6A is a partial side view of the tubular needle extended to carry the suture through the aperture of the jaw and pawl, in accordance with the invention;

FIG. 6B is a perspective view of the tubular needle extended to carry the suture through the aperture of the jaw and pawl, in accordance with the invention;

FIG. 6C is a perspective view of the suture captured by the pawl, in accordance with the invention;

FIG. 6D is a side view of the suture captured by the pawl, in accordance with the invention;

DETAILED DESCRIPTION OF THE PREFERRED EMBODIMENT

Figure 1A:
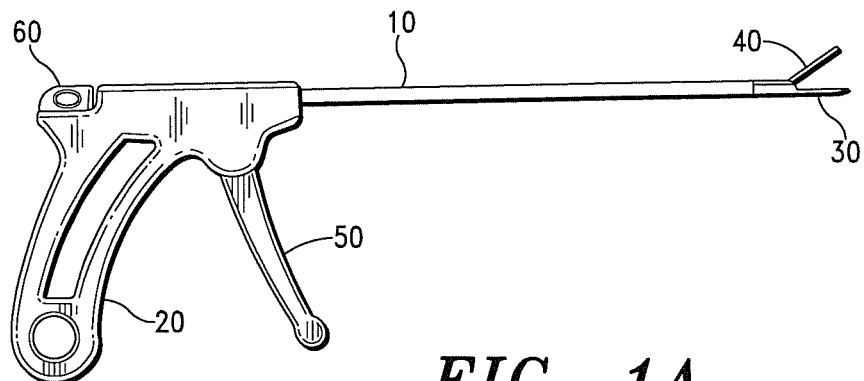
FIGS. 1A-1C show side views of a preferred embodiment of a suture passing device in various stages of deployment, in accordance with the invention.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with endoscopic procedures, the invention is not limited to such procedures. According to the invention, the apparatus, systems and methods of the invention can also be employed in connection with a multitude of other surgical procedures, including open surgical procedures.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10", as well as "greater than or equal to 10" is also disclosed.

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

The words used in the description to describe the invention and its various embodiments are to be understood not only in the sense of their commonly defined meanings, but to include by special definition in this specification the generic structure, material or acts of which they represent a single species.

The present invention relates generally to systems and methods for the driving of a needle or suture through or into body tissue (typically, the needle will be affixed to a suture that remains in the tissue) using a cannula, introducer or other minimally invasive means. The methods and devices described herein can be used in any number of medical procedures, including but not limited to, approximating tissue (e.g., bring separated tissue together), ligating tissue (e.g., encircling or tying off), and fixating of tissue (attaching tissue to another structure or different tissue).

Definitions

The terms "tissue" and "biological tissue" are used interchangeably herein, and mean and include mammalian biological tissue, such as, by way of example, human abdominal tissue.

The term "biological cavity", as used herein, means and includes any cavity or space in a mammalian tissue structure.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "endoscopy", as used herein, means and includes any minimally invasive surgical procedure conducted through at least one opening in a subject's body, including, but not limited to arthroscopy, laparoscopy, hysteroscopy and the like.

The terms "one configuration," "one embodiment," "one aspect," and "a configuration," "an embodiment" and "an aspect," as used herein, means that a particular feature, structure, or characteristic described in connection with the configuration may be included in at least one configuration and not that any particular configuration is required to have a particular feature, structure or characteristic described herein unless set forth in the claim.

The phrase "in one configuration" or similar phrases employed herein do not necessarily refer to the same configuration and, unless specifically stated, do not limit the inclusion of a particular element of the invention to a single configuration. The element may thus be included in other or all configurations discussed herein.

The term "substantially", as used herein, means and includes the complete or nearly complete extent or degree of an action, characteristic, property, state, structure, item, or result to function as indicated. For example, an object that is "substantially" enclosed would mean that the object is either completely enclosed or nearly completely enclosed. The exact allowable degree of deviation from absolute completeness may in some cases depend on the specific context, such that enclosing nearly all of the length of a lumen would be substantially enclosed, even if the distal end of the structure enclosing the lumen had a slit or channel formed along a portion thereof.

Use of the term "substantially" is equally applicable when used in a negative connotation to refer to the complete or near complete lack of an action, characteristic, property, state, structure, item, or result. For example, structure which is "substantially free of" a bottom would either completely lack a bottom or so nearly completely lack a bottom that the effect would be effectively the same as if it completely lacked a bottom.

The term "comprise" and variations of the term, such as "comprising" and "comprises," means "including, but not limited to" and is not intended to exclude, for example, other components, elements or steps.

The following disclosure is provided to further explain in an enabling fashion the best modes of performing one or more embodiments of the present invention. The disclosure is further offered to enhance the understanding and appreciation for the inventive principles and advantages thereof, rather than to limit in any manner the invention. The invention is defined solely by the appended claims, including any amendments made during the pendency of this application, and all equivalents of those claims as issued.

As indicated above, the present disclosure is directed to devices and methods for passing suture through biological tissue; particularly, biological tissues that are accessed via an endoscopic procedure.

As is well known in the art, both open and endoscopic surgical procedures often require sutures to ligate, join or otherwise treat tissue. Generally, suture needles with attached suture strands are grasped either manually or by forceps and passed through the desired work site so a knot can be tied. While the procedures are fairly uncomplicated in open surgery where most suture sites are readily accessible, in endoscopic procedures, where access to the work site is not readily available, the surgeon must use auxiliary devices to be able to grasp the suture strands and pass them through desired tissue.

Figure 1B:
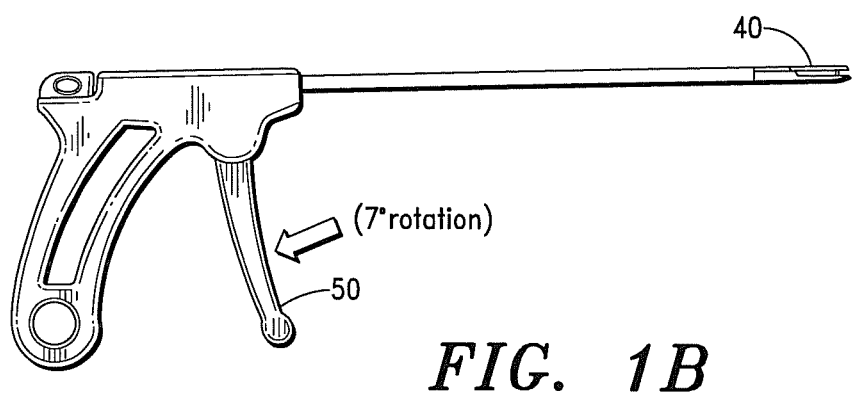

Referring now to the images where like elements are represented by like reference numerals. FIG. 1A illustrates a suture passing device, or instrument, of the present invention having an elongated tubular body 10, a hand grip 20, a tip 30, a jaw 40, an actuator 50 and a needle assembly 60. With actuator 50, a surgeon may seize and maintain tissue by movement of jaw 40 against tip 30 as shown in FIG. 1B. Using actuator 50, a surgeon may also deploy needle assembly 60 with tubular needle 70 carrying a suture 71 through tissue, as described below.

Figure 2A:
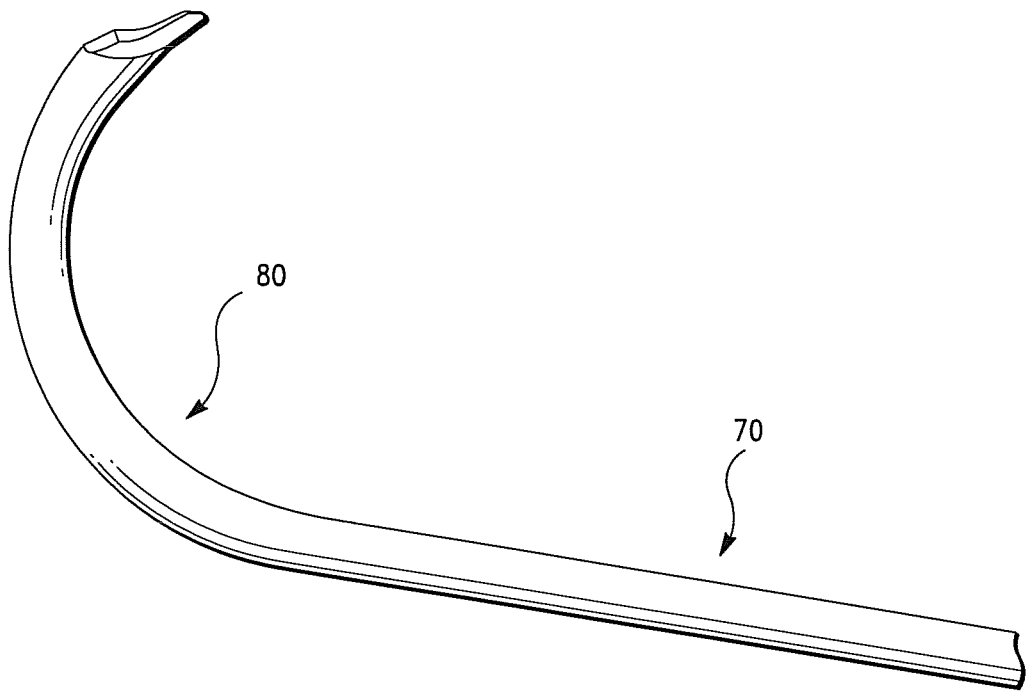
FIG. 2A is a side view of a preferred notchless tubular needle having a preformed memory shape, in accordance with the invention.
Figure 2B:
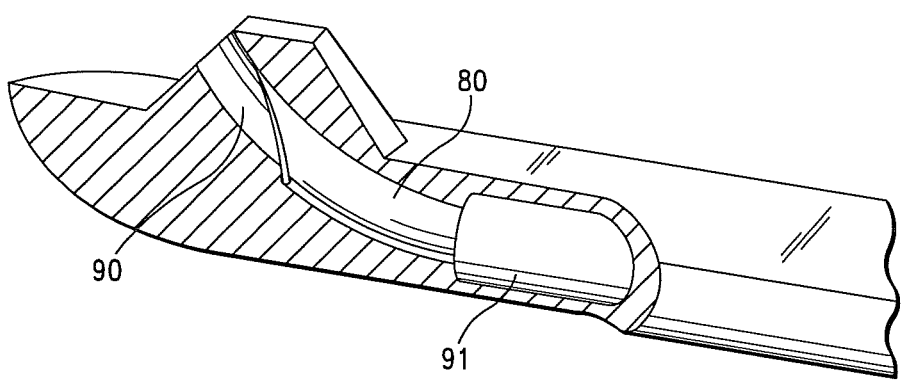
FIG. 2B is a side view of a preformed tubular needle in a sheathed, constrained state, in accordance with the invention.

FIG. 2A shows a preferred notchless tubular needle 70 in its natural state. As used throughout the specification, "notchless" shall refer to the absence of notches, slots, eyelets, or other such transverse openings for receiving suture as typically formed in needles of prior art suture passers. The distal end of the needle 80 is formed in a non-straight geometry. FIG. 2B shows a tubular needle 70 with the formed end 80 sheathed in a constraining channel 91. The channel for the needle also includes a curvilinear portion 90, or guide-path, that approximates the same geometry curve as the distal end of the tubular needle 80, thereby facilitating the consistent return of the needle 70 to its preformed curved shape each time the needle 70 exits the channel. The constrained state tubular needle 70 contained in the needle assembly 60 is loaded into the handle end of the tubular body 10 and advanced through a track in the tubular body 10.

Figure 1C:
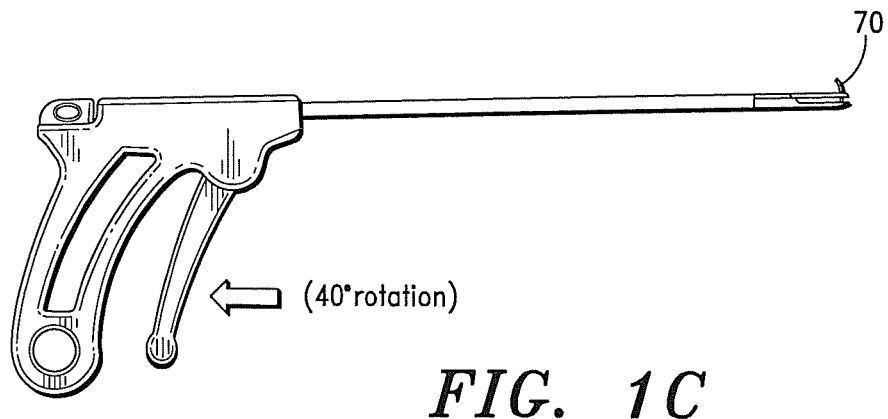

FIG. 1A illustrates a hand grip 20 and actuator 50 that provide articulation of jaw 40 relative to tip 30. The actuator 50 may be coupled to a return spring that biases the actuator 50 in the open position as seen in FIG. 1A. A surgeon may rotate actuator 50 approximately five to ten degrees, and preferably seven degrees, toward hand grip 20 to close jaw 40, as seen in FIG. 1B. A surgeon may then rotate actuator 50 approximately an additional thirty to forty degrees, and preferably thirty four degrees, towards hand grip 20 to activate tubular needle 70, extending it to its natural state 80, seen in FIG. 1C. The initial additional actuator rotation could require a significant resistance from a spring in the handle mechanism. This significant resistance on the actuator 50 acts as an indicator for the operator to know the tubular needle 70 is beginning to be deployed. Releasing the actuator 50 to its resting, open position returns tubular needle 70 to its constrained state 90 and then disengages jaw 40 to the open position.

Figure 3A:
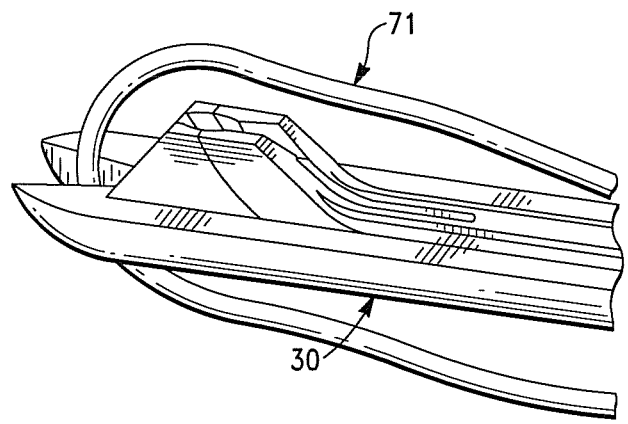
FIG. 3A is a side view of the preferred device's tip and suture prior to loading, in accordance with the invention.
Figure 3B:
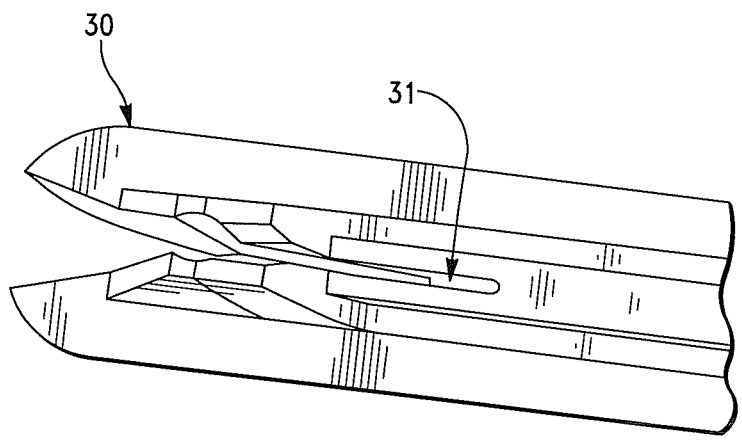
FIG. 3B is a perspective view of the tip with slot formed in a lower jaw, in accordance with the invention.
Figure 3C:
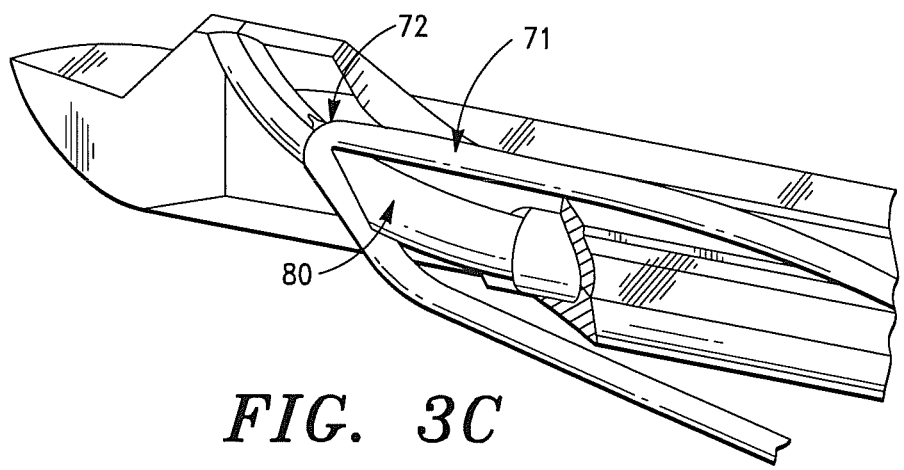
FIG. 3C is a perspective view of the tip, tubular needle, and suture, in accordance with the invention.

In FIG. 3A a loop of suture 71 is loaded into distal end of tip 30 with slot 31, seen in FIG. 3B. The slot 31 allows spring action for gripping the loop of suture 71 when the loop of suture is pulled into the tip 30. In one embodiment, shown in FIG. 3C, tubular needle 70 pierces the loop of suture 71 and creates a bifurcation 72 in the suture. When additional force is applied to the suture, the bifurcation 72 will advance along the shaft of the needle.

Figure 4A:
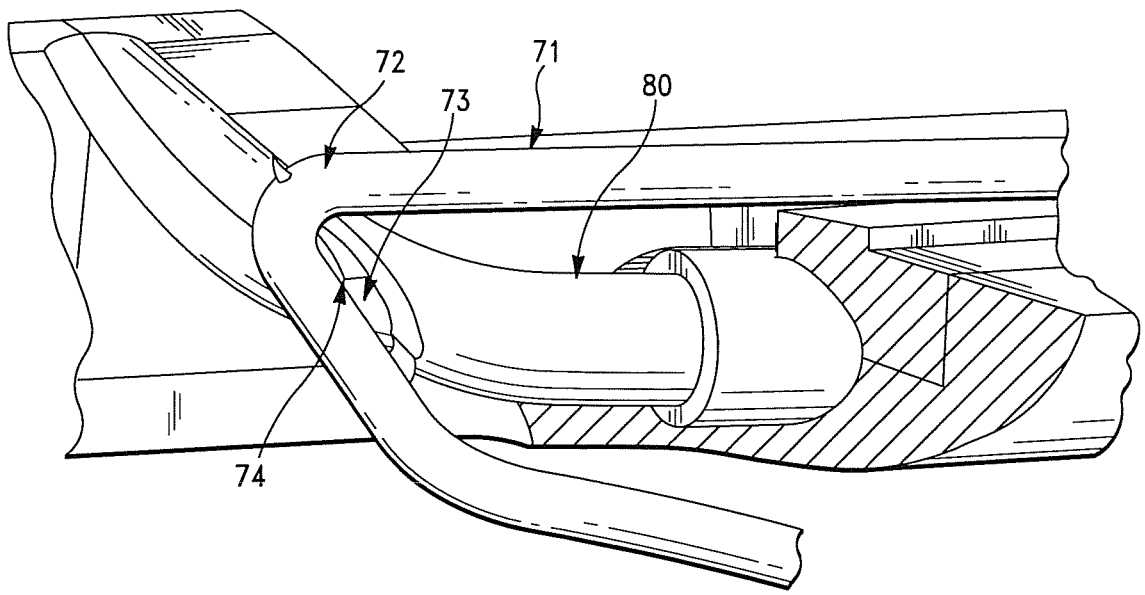
FIG. 4A is a perspective view of the tip, tubular needle, cleat, and suture, in accordance with the invention.
Figure 4B:
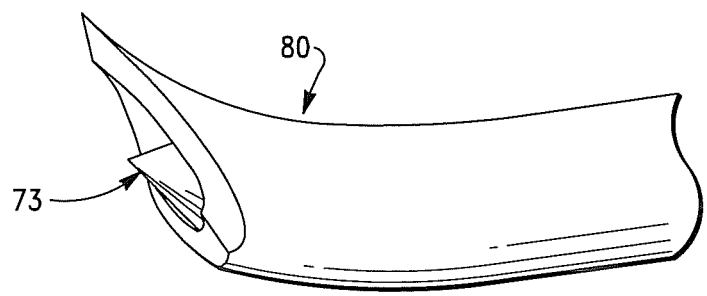
FIG. 4B is a perspective view of the device's tubular needle and prong cleat, in accordance with the invention.
Figure 4C:
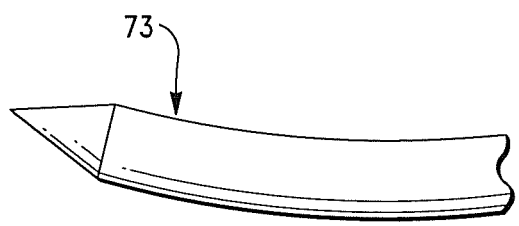
FIG. 4C is a perspective view of the device's prong cleat, in accordance with the invention.

To prevent the bifurcation 72 from advancing along the shaft of the needle, a prong cleat 73, illustrated in FIG. 4A is positioned to pierce the loop of suture 71 loop in second location. The pierce of the prong cleat may partially engage the thickness of the suture or create a second bifurcation 74 in the suture. The prong cleat 73 is a wire rod or tube housed within the lumen of the tubular needle with a sharp distal tip 73, shown in FIG. 4C, that slightly extends from the lumen of the tubular needle 70, as seen in FIG. 4B. The two piercing objects at different locations in the suture act in conjunction to stabilize the suture from advancing along the shaft of the needle.

Figure 5A:
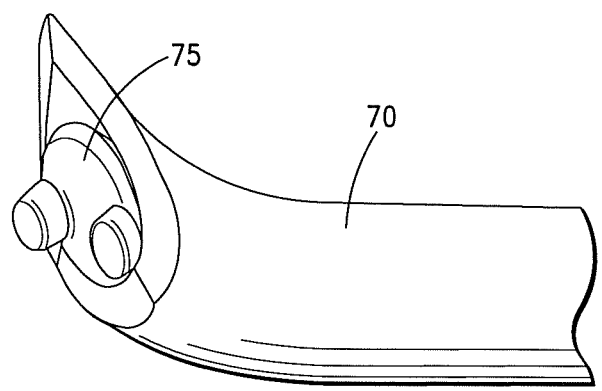
FIG. 5A is a perspective view of the device's tubular needle and lateral post cleat, in accordance with the invention.
Figure 5B:
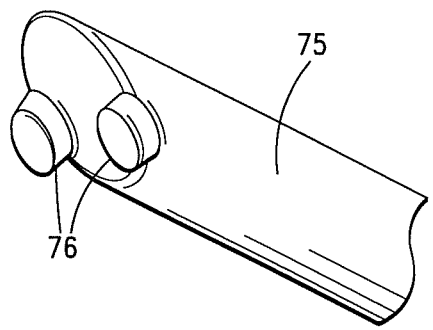
FIG. 5B is a perspective view of the device's lateral post cleat, in accordance with the invention.
Figure 5C:
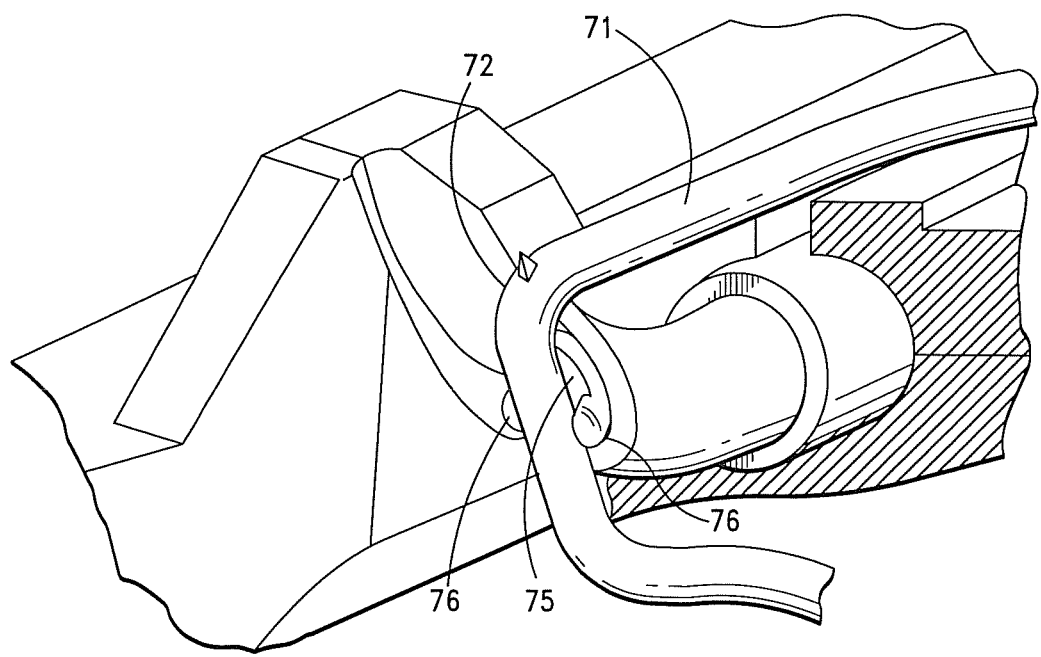
FIG. 5C is a perspective view of the device's tip, tubular needle, cleat, and suture, in accordance with the invention.

In another embodiment, shown in FIG. 5C, tubular needle 70 pierces the loop of suture 71 and creates a bifurcation 72 in the suture. When additional force is applied to the suture, the bifurcation 72 will advance along the shaft of the needle. To prevent the bifurcation 72 from advancing along the shaft of the needle, a lateral post cleat 75, illustrated in FIG. 5A is positioned to engage the bifurcated section of the suture, FIG. 5C. The body of the lateral post cleat 75 is housed inside the lumen of the tubular needle 70. Tension on the loop of suture 71 pulls the bifurcated legs of the suture against the lateral posts 76, preventing the suture 71 from sliding down the shaft of the needle.

FIG. 6B shows an aperture 41 in jaw 40 that tubular needle 70 and suture 71 pass through, as seen in FIG. 6A. A retractable pawl 42 is slidably positioned on jaw 40. Retractable pawl 42 includes a window that aligns with aperture 41 when extended forward in the open position. With tubular needle 70 and suture 71 deployed within aperture 41 by rotation of the actuator 50, the retractable pawl is then actuated to a reward position. The mechanism to actuate reward motion of the retractable pawl 42 may include a spring bias to provide a relatively constant load of the retractable pawl 42 against the deployed tubular needle 70 and suture 71.

Upon release of the actuator 50, a spring in the actuator mechanism returns the tubular needle 70 to the constraining channel 90. The spring bias of the retractable pawl 42 allows the tubular needle 70 to return, yet maintains a grip on the suture 71 and pulls it in a reward movement to become captured in between the proximal edge 44 of the aperture 41 in the jaw 40 and distal edge of the pawl window, as is shown in FIGS. 6C and 6D. Complete release of the actuator 50 disengages the jaw 40 to the open position, thus completing the passage of suture 71 through the tissue.

Figure 7A:
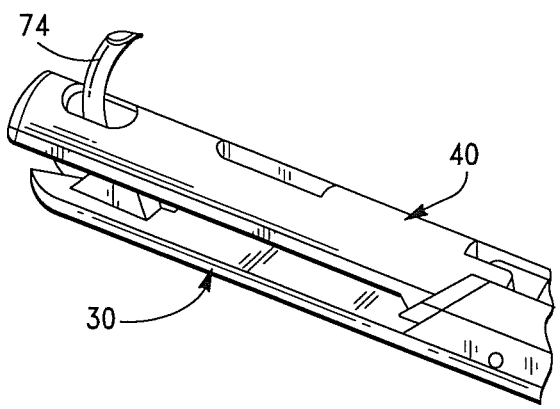
FIG. 7A is a perspective view of a preferred embodiment having two tubular needles and jaw, in accordance with the invention.

In some variations, the suture passing device may be composed to have two or more tubular needles 70. In one embodiment, the suture passing device can throw more than one segment of suture 71 through tissue simultaneously. The segments of suture being passed by multiple tubular needles 70 may be attached to form a continuous loop of suture, thus enabling the formation of a desired suture pattern, i.e. horizontal mattress stitch. FIG. 7A shows a left tubular needle 74 and a right tubular needle 75 after being simultaneously released to their natural states 80. In another embodiment, the device may throw two or more tubular needles 70 through tissue sequentially.

Figure 7B:
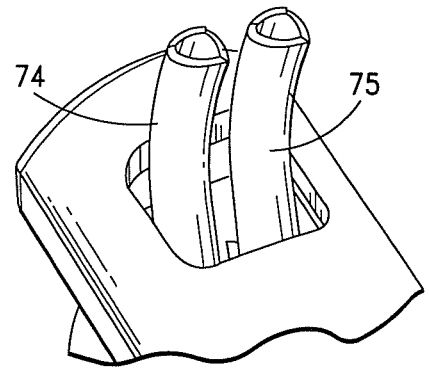
FIG. 7B is a perspective view of the left tubular needle extended in the jaw, in accordance with the invention.
Figure 7C:
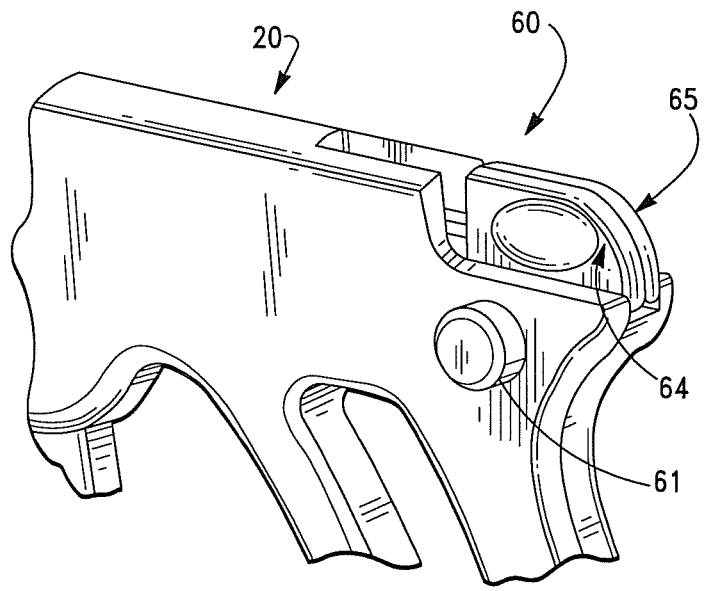
FIG. 7C is a side view of the device's hand grip, toggle switch and needle assemblies, in accordance with the invention.

The segments of suture being passed by multiple tubular needles 70 may be attached to form a continuous loop of suture, thus enabling the formation of a desired suture pattern, i.e. horizontal mattress stitch. The handle mechanism could be configured to deploy the left needle assembly 64 and right needle assembly 65 independently. FIG. 7C shows the handle mechanism with a switch 61 to toggle and engage one needle assembly at a time in the drive track 60. Suture 71 could be loaded to the tips of both needle assemblies (as described above) before entering the device down the cannula. With the switch 61 toggled to engage the left needle assembly 64, the jaw could be actuated to grasp a desired location of tissue and the left tubular needle 74 deployed to pass suture and capture suture in a first tissue location. FIG. 7B shows a left tubular needle 74 released to its natural state 80 (suture is not shown in image).

Figure 7D:
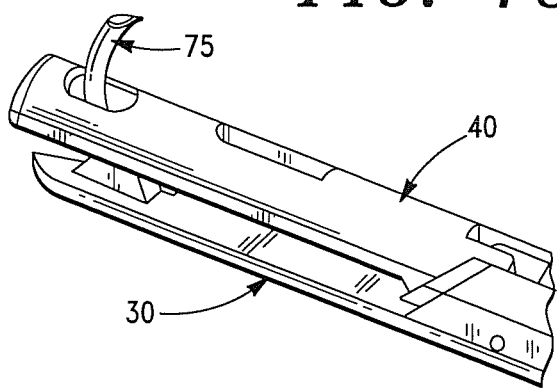
FIG. 7D is a perspective view of the right tubular needle extended in the jaw, in accordance with the invention.

Fully releasing the actuator 50 returns the left tubular needle 74 to its constrained state 90 and disengages jaw 40. The suture passing instrument may then be repositioned to a second desired tissue location. A surgeon could then select right needle assembly 65 by toggling the needle track 60 on the instrument's body 10, as seen in FIG. 7C. With the switch 61 toggled to engage the right needle assembly 65, the jaw could be actuated to grasp a second desired location of tissue and the right tubular needle 75 deployed to pass suture and capture suture in a second tissue location. FIG. 7D shows a right tubular needle 75 released to its natural state 80 (suture is not shown in image). Fully releasing the actuator 50 returns the right tubular needle 75 to its constrained state 90 and disengages jaw 40 from tissue. The suture passing instrument may then be removed from the cannula to expose the two ends of the suture.

Figure 8A:
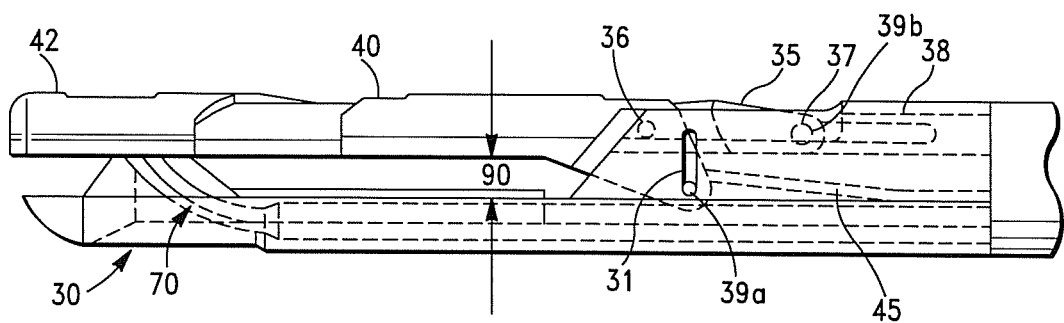
FIG. 8A is a side view of the tip with slot and floating pivot in the collapsed state, in accordance with the invention.
Figure 8B:
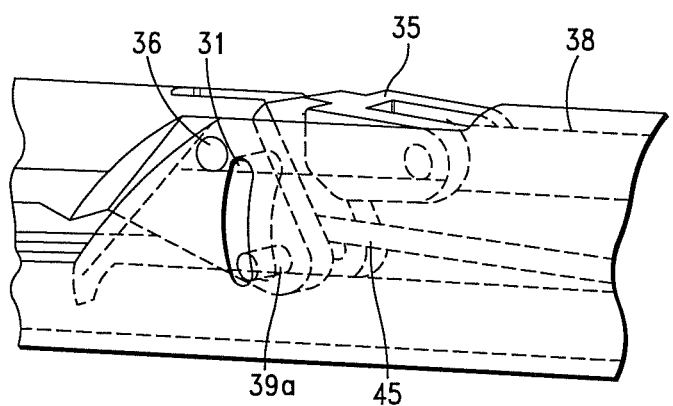
FIG. 8B is a perspective view of the mechanism for the floating pivot, in accordance with the invention.
Figure 8C:
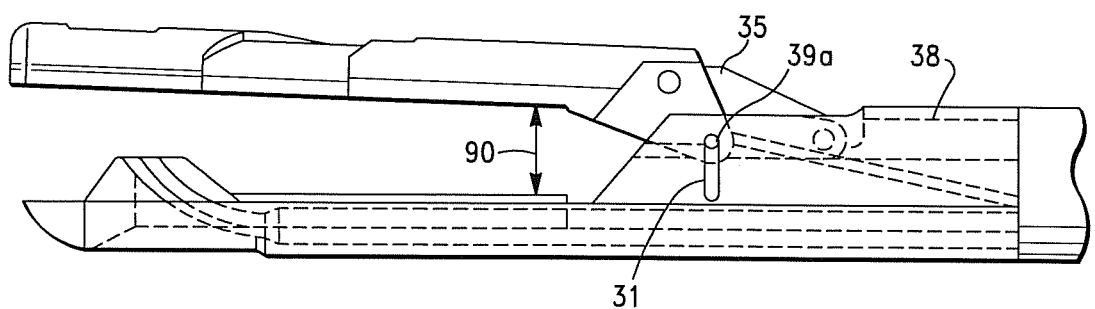
FIG. 8C is a side view of the tip with slot and floating pivot in the expanded state, in accordance with the invention.

In yet another embodiment, the device described above includes floating a pivot mechanism as shown in FIGS. 8A-8C to facilitate a lower profile when the jaw 40 and tip 30 are separated. The jaw 40 includes a pivot interface 36 with linkage 35. At the opposite end of linkage 35 is another pivot interface 37 that joins linkage 35 and drive rod 38. The tip 30 includes a slot 31 in which a pin 39a slides within. The pin 39a is fixed to jaw 40. Axial movement of drive rod 38 in relation to the tip 30 causes jaw 40 to rotate about pin 39a in relationship to the tip 30. A leaf spring 45 exerts a load against the pin 39a in a direction to bias the pin against the lower end of slot 31, thus resulting in the jaw 40 in a collapsed state as shown in FIG. 8A. The gap 90 between the inner surfaces of the tip 30 and jaw 40 is minimized.

The collapsed state is advantageous for providing a minimum profile for advancing the device through an access cannula. In some embodiments, the device can be configured to be advanced into the through an access cannula having a diameter in the range of 2.0-15 mm, more preferably, in the range of 5.0-8.0 mm.

When the tip 30 and jaw 40 are positioned unto tissue, advancement of the drive rod 38 causes the jaw 40 to rotate about pin 39a to clamp onto the tissue. The resisting force of the tissue to compression between tip 30 and the jaw 40 causes a force on the inner surface of the jaw 40. If the force on the inner surface of the jaw 40 exceeds the force of the leaf spring 45 to hold the pin 39a against the lower end of slot 31, the pin will ride up the slot 31, and effectively increase the gap 90 between the inner surfaces of tip and the jaw 40, as shown in FIG. 8C. To increase the gap 90 at the axillia acts to distribute the clamp force along the length of the jaw 40. The distribution of clamp force enables the distal end of jaw 40 to achieve a position in closer proximity to tip 30.

In some embodiments, gap 90 between the inner surfaces of tip and the jaw 40 comprise a width in the range of 0.5-5.0 mm, more preferably, the gap 90 between the inner surfaces of tip and the jaw 40 comprise a width in the range of 1.5-3.3 mm.

Figure 9A:
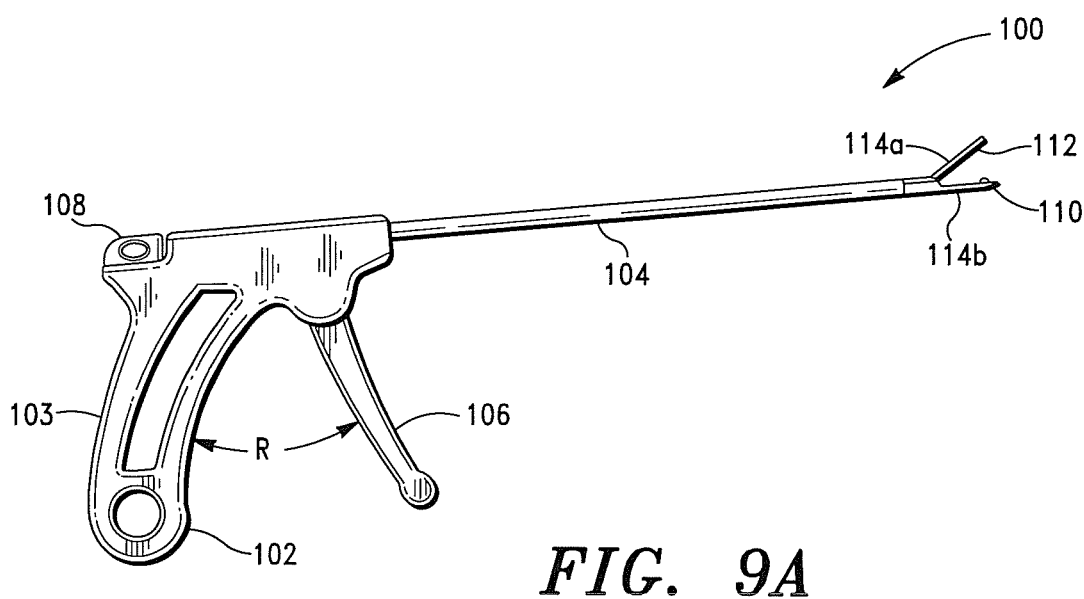
FIGS. 9A-9C show side views of another embodiment of a suture passing device in various stages of deployment, in accordance with the invention.
Figure 9B:
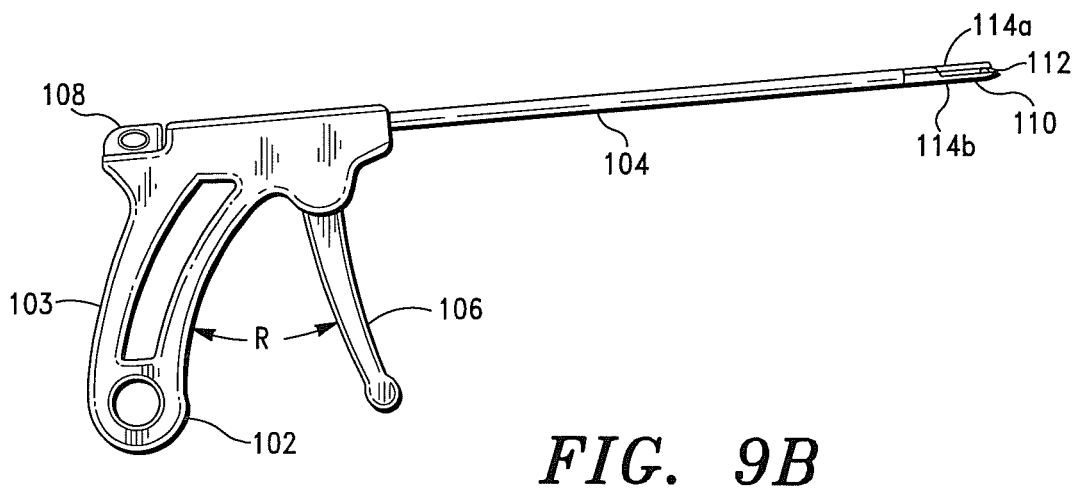
Figure 9C:
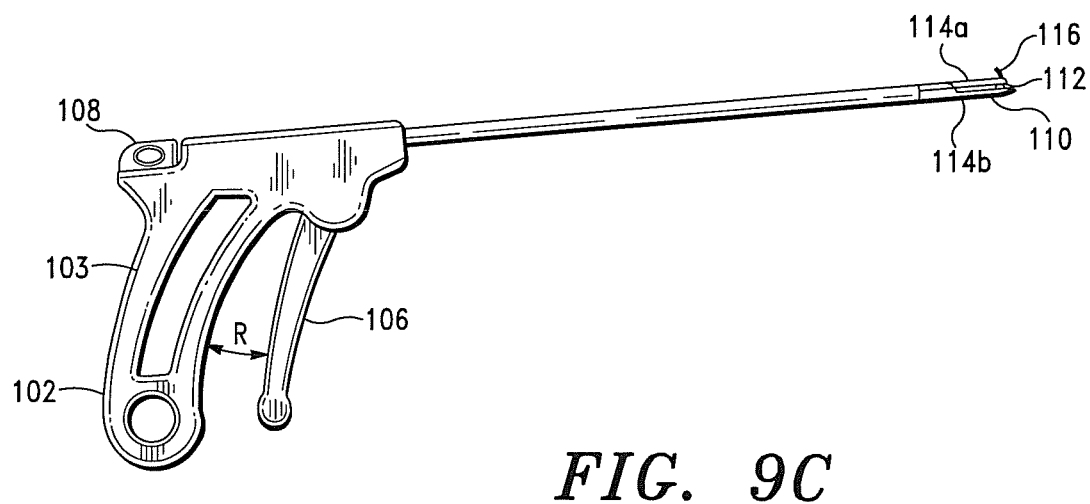

Referring now to FIGS. 9A-9C, there is shown another embodiment of a suture passing device 100 at various stages of actuation. As illustrated in FIG. 9A, the suture passing device 100 of the present invention comprises a hand grip 102 in operative communication with elongated tubular body or member 104 having a distal end 110.

As further illustrated in FIG. 9A, hand grip 102 comprises a proximal end 103, an actuator 106 and a needle assembly 108, and elongated tubular member 104 comprises a jaw mechanism 112 having top and bottom members 114a, 114b disposed proximate the elongated tubular member 104 distal end 110. In a preferred embodiment, the jaw mechanism 112 top and bottom members 114a, 114b comprise proximal and distal ends.

In a preferred embodiment, the jaw mechanism 112 of the suture passing device 100 similarly comprises the floating pivot mechanism and pivot interface discussed above and shown in FIGS. 8A-8C to facilitate a lower profile when the top and bottom members 114a, 114b of jaw mechanism 112 are separated and axial articulation of the top and bottom members 114a, 114b.

In the noted embodiments, the jaw mechanism 112 preferably comprises first and second pins 39a, 39b, the proximal end of the jaw mechanism 112 top member 114a comprises first and second pin lumens, and the proximal end of the jaw mechanism 112 bottom member 114b comprises a third pin lumen and a pin slot 31.

Preferably, the first pin lumen and the pin slot 31, and the second and third pin lumens are in axial alignment.

In a preferred embodiment, the jaw mechanism 112 top member 114a first pin lumen and the bottom member 114b pin slot 31 are configured to receive and position the jaw mechanism 112 first pin 39a, wherein, when the jaw mechanism 112 first pin 39a is received by and positioned in the jaw mechanism 112 top member 114a first pin lumen and the bottom member pin slot 31, the jaw mechanism 112 top member 114a is allowed to vertically articulate with respect to the jaw mechanism 112 bottom member 114b.

In a preferred embodiment, the jaw mechanism 112 top member 114a second pin lumen and the bottom member 114b third pin lumen are configured to receive and position the jaw mechanism 112 second pin 39b, wherein, when the jaw mechanism 112 second pin 39b is received by and positioned in the jaw mechanism 112 top member 114a second pin lumen and the bottom member third pin lumen, the jaw mechanism 112 top member 114a is allowed to axially articulate with respect to the jaw mechanism 112 bottom member 114b.

According to the invention, any of the embodiments of the jaw mechanism described herein can comprise the floating pivot mechanism and pivot interface discussed above and shown in FIGS. 8A-8C.

According to the invention, the suture passing device 100 can be used to capture and maintain biological tissue by positioning the jaw mechanism 112 of the suture passing device 100 proximate the tissue and applying a first radial force on the actuator 106 to transition the top and bottom members 114a, 114b of jaw mechanism 112 from an open configuration to a closed configuration, as shown in FIG. 9B. A second radial force can also be applied to actuator 106 to deploy needle assembly 108 comprising a tubular needle 116 having a suture 500 attached thereto into and through the tissue as shown in FIG. 9C, as discussed in detail below.

In a preferred embodiment, the actuator 106 provides axial articulation of top member 114a relative to bottom member 114b of jaw mechanism 112. In some embodiments, the actuator 106 can be coupled to a return spring (not shown) that biases the actuator 106 in the open configuration shown in FIG. 9A.

In some embodiments, actuator 106 can be rotated, as denoted by arrow R', in the range of 3°-30°, more preferably, the actuator 106 can be rotated in the range of 7°-10° toward the hand grip 102 to transition the top and bottom members 114a, 114b of jaw 112 from an open configuration to a closed configuration, as shown in FIG. 9B.

Figure 10A:
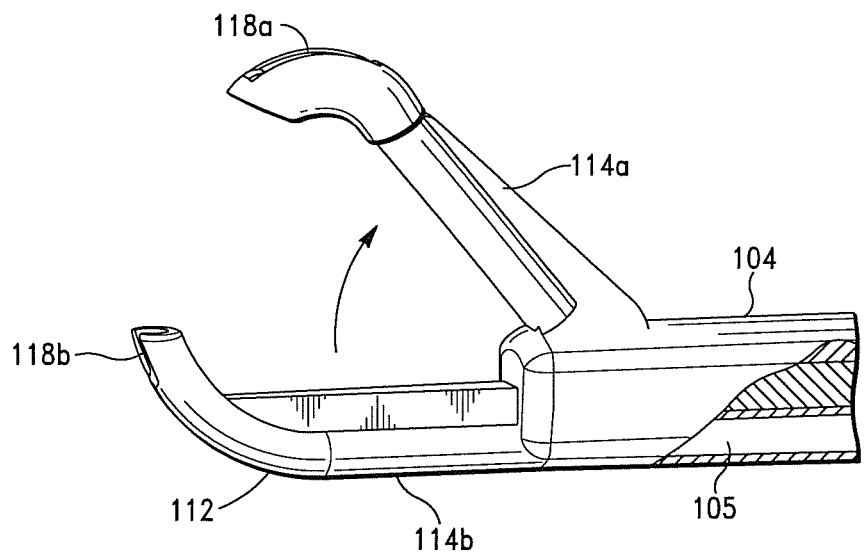
FIG. 10A is a side plan partial sectional view of the device's elongated member distal tip and jaw mechanism prior to loading suture, in accordance with the invention.
Figure 10B:
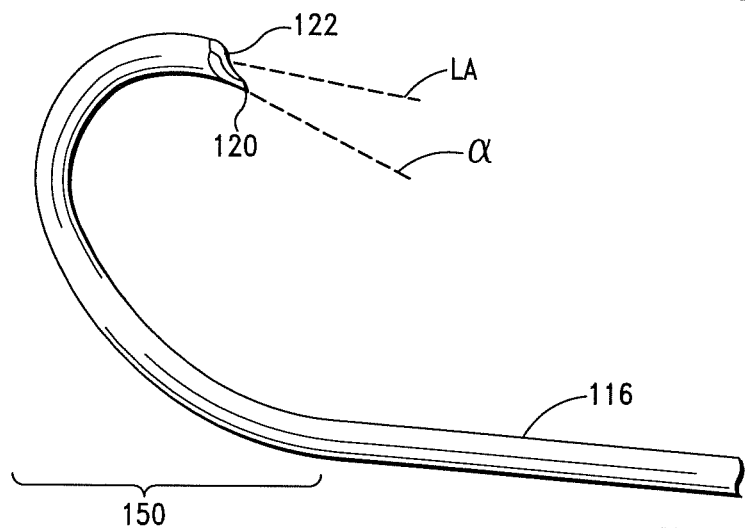
FIG. 10B is a side view of a preformed tubular needle, in accordance with the invention.
Figure 10C:
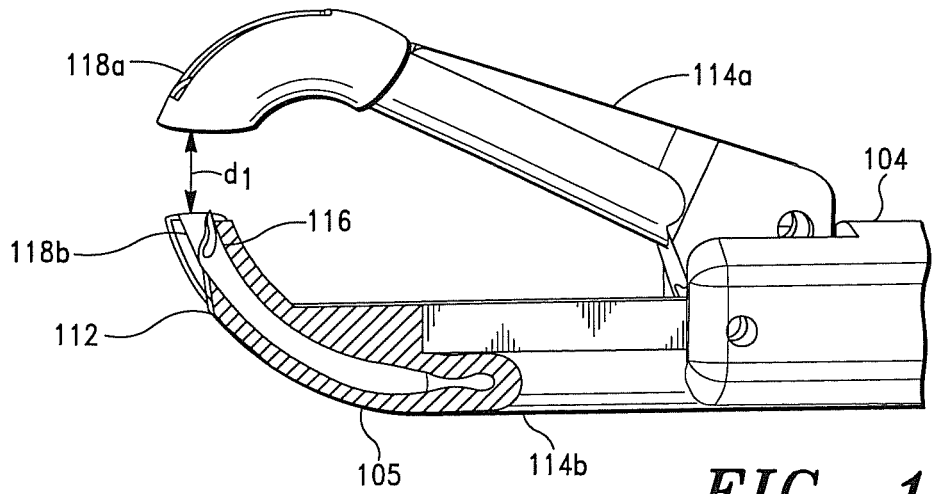
FIG. 10C is a side plan partial sectional view of a preformed tubular needle retracted and constrained in the guide channel of the bottom member, and the jaw mechanism set at a determined gap distance, in accordance with the invention.

In some embodiments, the actuator 106 can be further rotated in the direction denoted by arrow R, in the range of 20°-60°, more preferably, in the range of 34°-45° towards hand grip 102 to slidably translate the tubular needle 116 shown in FIG. 10C into and through the internal lumen 105 towards the jaw mechanism 112 of elongated tubular member 104, as shown in FIG. 9C.

In some embodiments of the invention, the actuator 106 of the hand grip 102 comprises a spring loaded mechanism that is configured to provide a resistance force in the range of 10-110 N, more preferably, a resistance force in the in the range of 25-75 N on the actuator 106 to provide tactile feedback for the operator to indicate that the tubular needle 116 is slidably translating into and through the jaw mechanism 112.

According to the invention, the actuator 106 is configured to transition back to a resting, open configuration in the absence of radial force, whereby, the tubular needle 116 slidably transitions back to a constrained state and top and bottom members 114a, 114b of jaw mechanism 112 transition back to an open position.

Referring now to FIG. 10A, there are shown top and bottom members 114a, 114b of jaw mechanism 112 in an open configuration. As illustrated in FIG. 10A, the top member 114a comprises a guide channel 118a and the bottom member 114b comprises a guide channel 118b. In a preferred embodiment, the guide channels 118a, 118b are sized and configured to receive tubular needle 116 of the invention therein.

As further illustrated in FIG. 10A, in a preferred embodiment, guide channel 118b is in aligned communication with the elongated member 104 internal lumen 105.

Figure 11A:
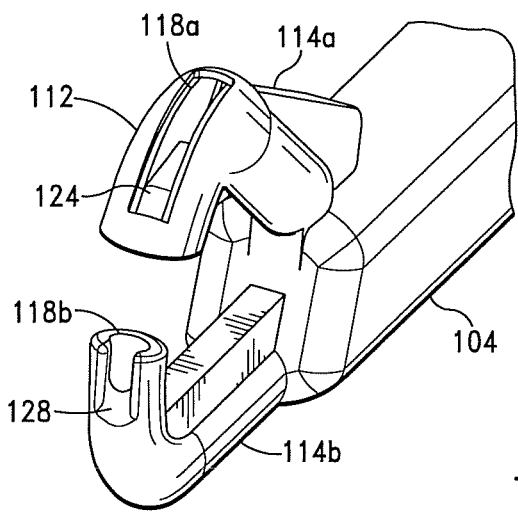
FIG. 11A is a perspective view of the device's elongated member distal tip and jaw mechanism showing the pawl feature, in accordance with the invention.
Figure 11B:
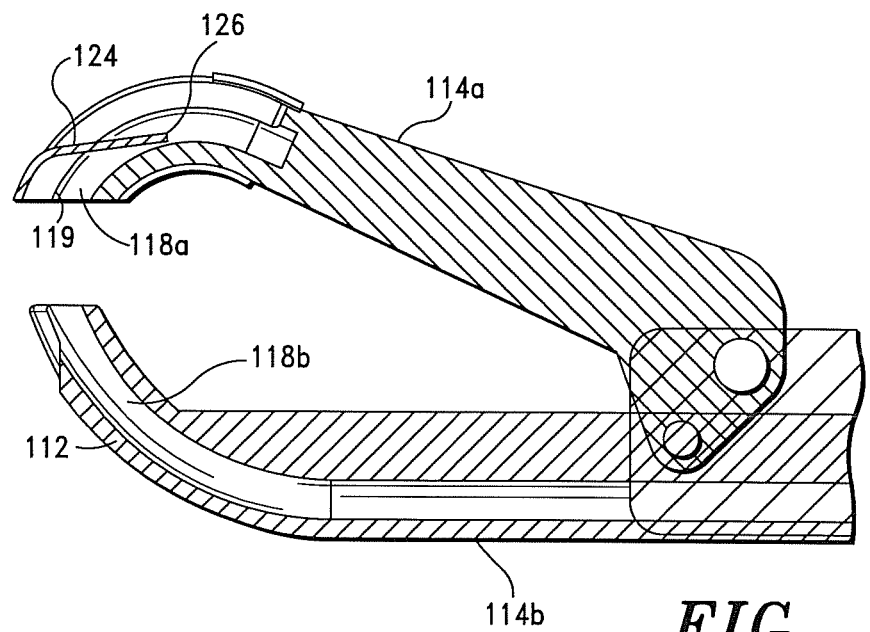
FIG. 11B is a side plan sectional side view of the elongated member distal tip and jaw mechanism showing the track for the needle, in accordance with the invention.
Figure 11C:
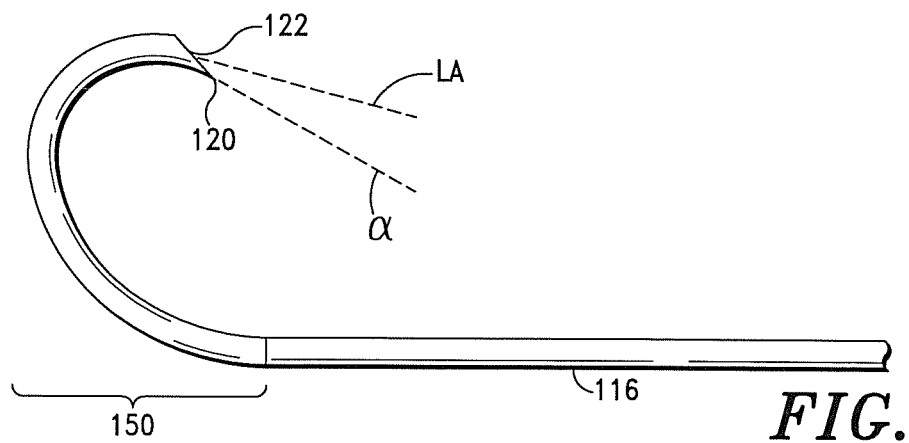
FIG. 11C is a side view of the tubular needle with two segments to match the track profile, in accordance with the invention.

Referring now to FIGS. 10B and 11C, there is shown tubular needle 116 in a first natural state comprising a distal end 120 an internal lumen 122. As illustrated in FIG. 10B, the tubular needle 116 comprises a formed curvilinear portion 150.

In some embodiments, the tubular needle 116 comprises multiple curvilinear sections 150 to slidably translate into and through the guide channels 118a, 118b. According to the invention, the curvilinear portion 150 of the tubular needle can comprise any suitable shape where 6% strain is not exceeded.

In a preferred embodiment, the tubular needle 116 comprises nickel-titanium alloy (Nitinol®) and is configured to transition from a constrained state to an unconstrained or natural state. As illustrated in FIG. 10B, in a preferred embodiment, the unconstrained state tubular member 116 comprises formed curvilinear portion 150.

As shown in FIG. 10C, in some embodiments, the tubular needle 116 is adapted to deform into a constrained state when the curvilinear portion 150 of the tubular needle 116 is advanced through the elongated tubular member 104 internal lumen 105 and into guide channel 118b of the jaw mechanism 112 bottom member 114b.

In some embodiments, the curvilinear portion 150 of the tubular needle 116 is adapted to reassume a curvilinear shape upon further advancement out of guide channel 118b and into and through guide channel 118a of the jaw mechanism 112 top member 114a.

In some embodiments, the tubular needle 116 comprises a hollow and rigid needle. In some embodiments, the tubular needle 116 comprises geometry where the area moment of inertia about the neutral bending axis is in the range of $20.0 \times 10^{-9}$-$300.0 \times 10^{-9}$ inches to the $4^{th}$ power, more preferably, the tubular needle comprises a geometry where the area moment of inertia about the neutral bending axis in the range of $25.0 \times 10^{-9}$-$75.0 \times 10^{-9}$ inches to the $4^{th}$ power, which allows the tubular needle 116 to be driven into biological tissue with minimal deflection or skiving.

According to the invention, the tubular needle 116 distal end 120 can comprise various configurations, including, but not limited to, a beveled, curved and serrated edge, which is configured to pierce through biological tissue.

In a preferred embodiment, the tubular needle 116 distal end 120 comprises a beveled edge having an angle "α" in the range of approximately 1°-90° with respect to the longitudinal axis "LA" of the tubular needle 116. More preferably, the angle "α" of the beveled distal end 120 is in the range of approximately 45°-90°.

In some embodiments, the tubular needle 116 comprises a disposable member that is replaced after a single use. In some embodiments, the tubular needle 116 comprises a permanent reusable member of the suture passing device 100.

Referring now to FIG. 10C there are shown top and bottom members 114a, 114b of jaw mechanism 112 in a closed configuration having tubular needle 116 disposed in the guide channel 118b of bottom member 114b. As illustrated in FIG. 10C, the top and bottom members 114a, 114b of jaw mechanism 112 comprise a reciprocating curvilinear configuration that is configured to align guide channels 118a, 118b and, thereby, approximate the same curvilinear shape or configuration as the formed curvilinear portion 150 of the tubular needle 116 when the jaw mechanism 112 is in a closed configuration.

As further illustrated in FIG. 10C, when the top and bottom members 114a, 114b of jaw mechanism 112 are in a closed configuration the top and bottom members 114a, 114b are configured to be partially closed at a set distance $d_1$ from each other.

In some embodiments, the top and bottom members 114a, 114b are configured to be partially closed at a set distance $d_1$ in the range of 0-5.0 mm, more preferably, at a set distance $d_1$ in the range of 1.0-2.0 mm. In some embodiments, the set distance $d_1$ is configured to be modulated by a user.

In some embodiments, the top and bottom members 114a, 114b are configured to fully close to facilitate passage through an access cannula.

In a preferred embodiment, the needle assembly 108 and the tubular needle 116 in communication therewith are engaged to the proximal end 103 of hand grip 102 and the tubular needle 116 is slidably transitioned into and through the elongated tubular member 104 internal lumen 105 in a constrained state.

Referring now to FIGS. 11A and 11B, there is shown pawl 124 of the top member 114a of jaw mechanism 112. As illustrated in FIGS. 11A and 11B, the pawl 124 comprises a distal end 126 and intersects the guide channel 118a and, hence, the path defined by the guide channel 118a.

Figure 12A:
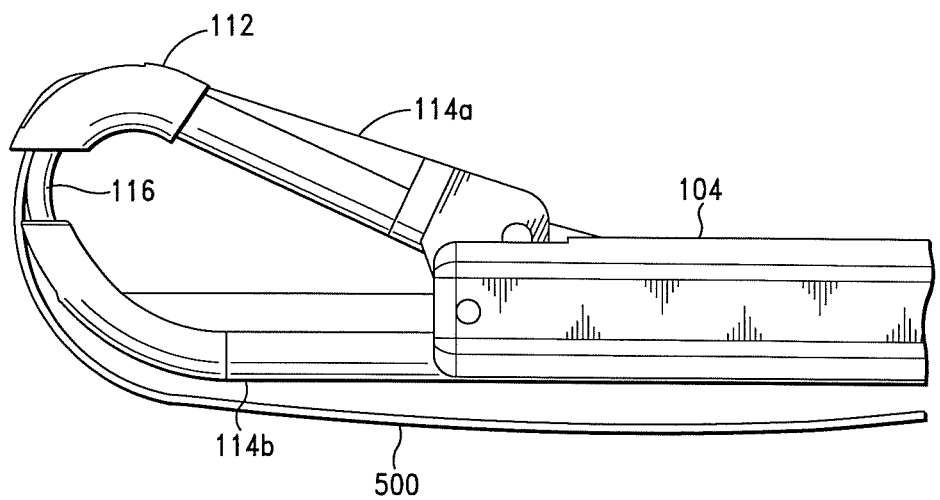
FIG. 12A is a perspective view of the elongated member distal tip, jaw mechanism, and tubular needle extended with suture, in accordance with the invention.
Figure 12B:
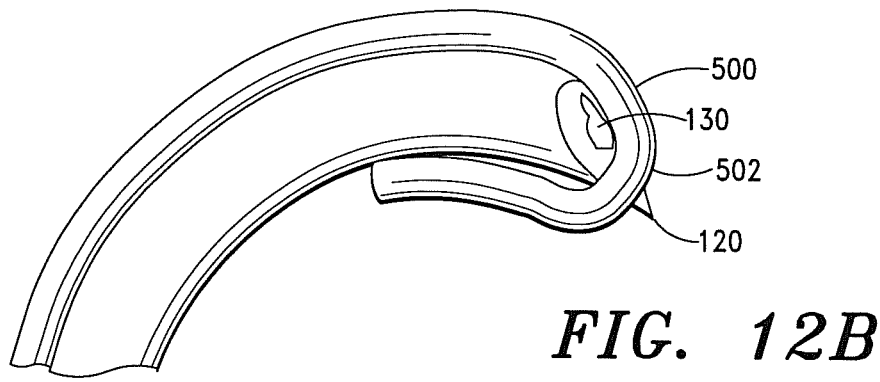
FIG. 12B is a perspective view of the device's tubular needle and prong cleat member extended to carry the suture through the aperture of the jaw mechanism and pawl, in accordance with the invention.

As further illustrated in FIG. 11A, the bottom member 114b of jaw mechanism 112 comprises a capture lip 128 that is configured to facilitate the capture of a portion of suture 500 shown in FIG. 12B.

Figure 12C:
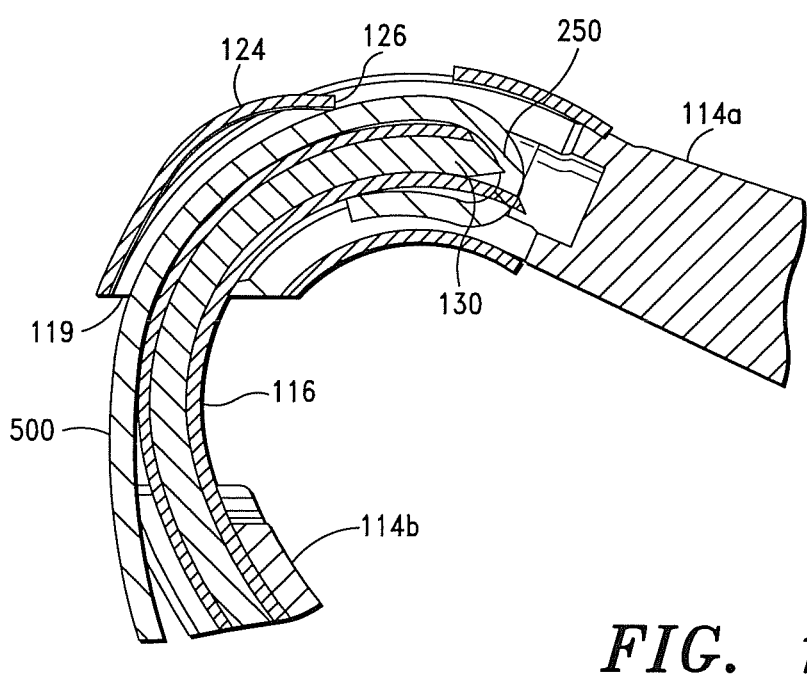
FIG. 12C is a side plan sectional view of the elongated member distal tip, jaw mechanism, tubular needle and prong cleat member, and the suture loaded on the tubular needle distal end, in accordance with the invention.

In some embodiments, the pawl 124 may be used as a suture capturing mechanism. Referring now to FIG. 12C, when the tubular needle 116 guides the suture 500 into the guide channel 118a the pawl 124 is deflected, which allows the suture 500 to be guided beyond the distal end 126 of the pawl 124 by tubular needle 116.

According to the invention, when the tubular needle 116 is retracted from the guide channel 118a past the pawl 124, the distal end 126 of pawl 124 exerts a closure force on the suture 500 and captures the suture 500 between the pawl 124 distal end 126 and the inner wall 119 of guide channel 118a.

In some embodiments, the distal end 126 of pawl 124 exerts a closure force in the range of 10-110 N, more preferably, a closure force in the range of 25-75 N.

Referring now to FIGS. 12B and 12C, there is shown suture 500 having a distal end 502 that is loaded onto the distal end 120 of the tubular needle 116. As illustrated in FIGS. 12B and 12C, the distal end 120 of tubular needle 116 is configured to pierce at least a portion of suture 500.

As further illustrated in FIG. 12B, in a preferred embodiment, the distal tip 120 of tubular needle 116 is configured to pierce and form a bifurcation 250 in the suture 500.

As illustrated in FIGS. 12B and 12C, in some embodiments, the tubular needle 116 comprises a cleat member 130 having a piercing distal end 132. In a preferred embodiment, the cleat member 130 is at least partially disposed in the tubular needle 116 internal lumen 130.

As further illustrated in FIGS. 12B and 12C, the cleat member 130 is positioned and configured to pierce and engage at least a portion of the suture 500. In some embodiments, the cleat member 130 is positioned and configured to generate an additional bifurcation in at least a portion of the suture 500.

In a preferred embodiment, the cleat member 130 comprises a wire rod or tube housed within the tubular needle 116 internal lumen 122 that partially extends or protrudes distally outward from the tubular needle 116 internal lumen 122. In a preferred embodiment, the tubular needle 116 distal end 120 and the cleat member 130 distal end 132 pierce and engage suture 500 at two (2) predetermined locations on the suture 500 to secure the suture 500 thereto.

Figure 13A:
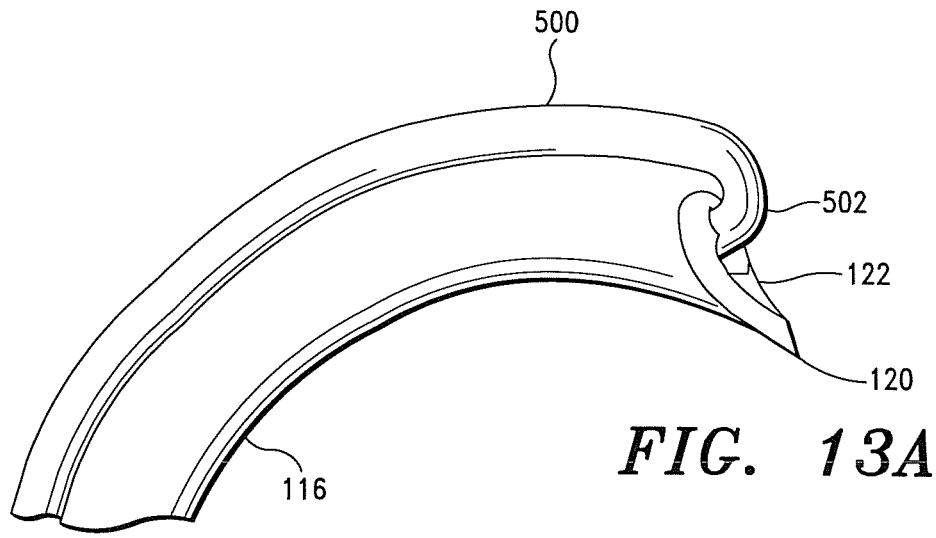
FIG. 13A is a perspective view of the device's tubular needle with a front loaded suture, in accordance with the invention.
Figure 13B:
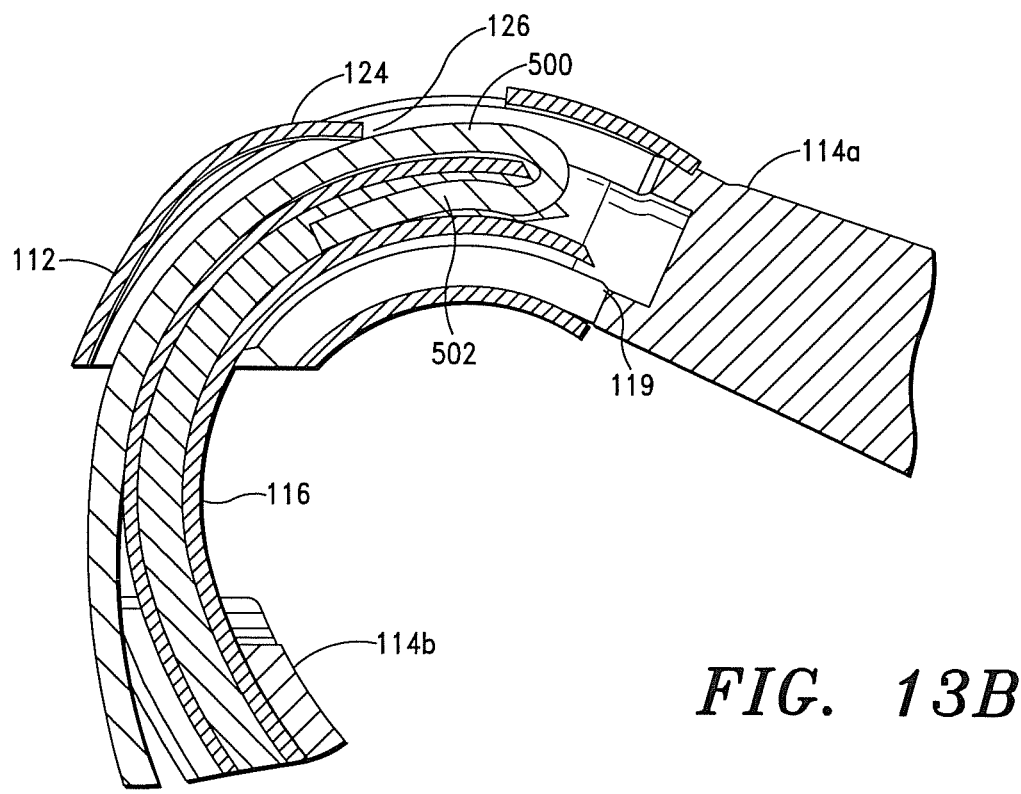
FIG. 13B is a side plan sectional view of the elongated member distal tip, jaw mechanism, and tubular needle with a front loaded suture, in accordance with the invention.

Referring now to FIGS. 13A and 13B, there is shown distal end 502 of suture 500 front loaded into the internal lumen 122 of the tubular needle 116 distal end 120. As shown in FIGS. 13A and 13B, the bend in the distal end 502 of the suture 500 provides a strain relief section that functions to releasably secure the distal end 502 of the suture 500 to the tubular needle 116 distal end 120 for penetration and advancement into biological tissue. When the tubular needle 116 is retracted from biological tissue, at least a portion of suture 500 is captured and retained by the biological tissue.

As illustrated in FIG. 13B, in some embodiments, the suture 500 distal end 502 is engaged by the distal end 126 of pawl 124, wherein the suture 500 distal end 502 captured between the distal end 126 of pawl 124 and the inner wall 119 of the guide channel 118a.

Figure 14:
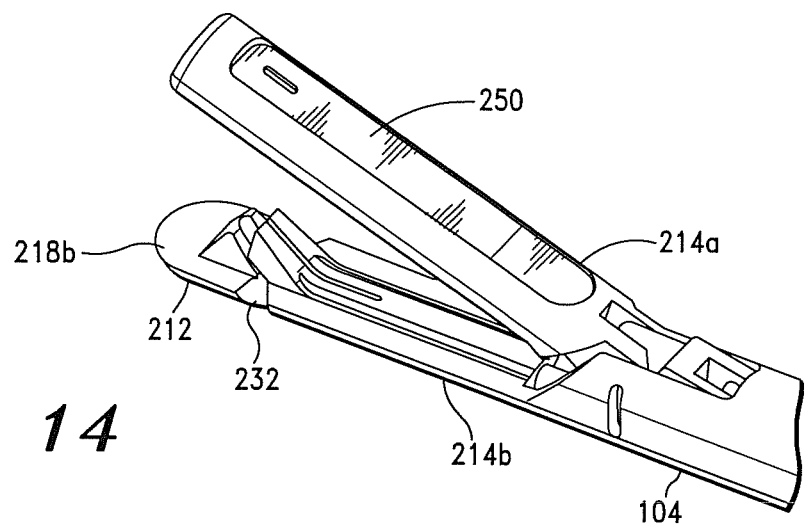
FIG. 14 is a perspective view of another embodiment of the jaw mechanism in the open position with the tubular needle fully retracted, showing the needle shield secured to the jaw mechanism top member, in accordance with the invention.
Figure 15:
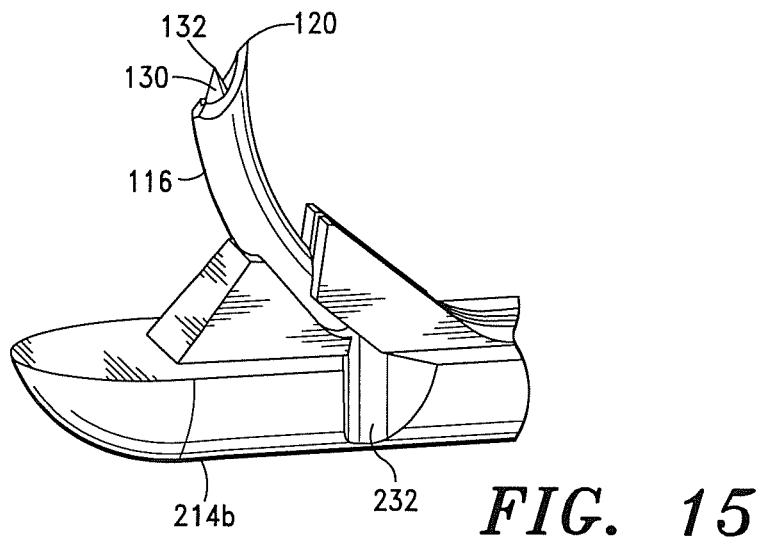
FIG. 15 is a perspective view of tubular needle partially exposed, in accordance with the invention.
Figure 16:
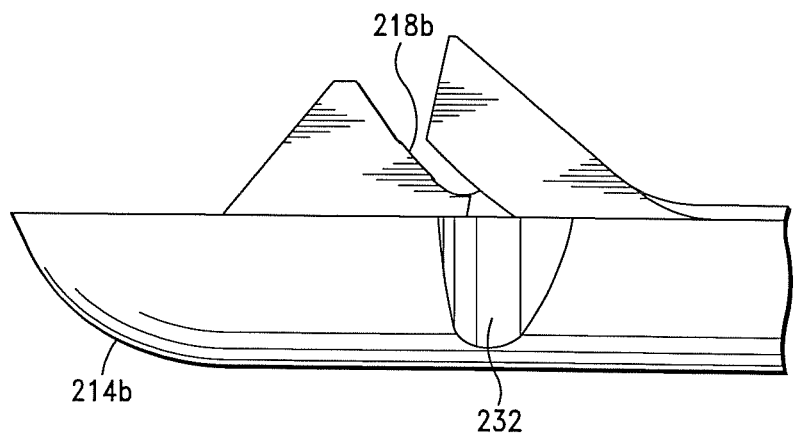
FIG. 16 is a side view of the jaw mechanism bottom member revealing the laterally oriented suture loading slot, in accordance with the invention.

Referring now to FIGS. 14-19, there is shown another embodiment of jaw mechanism 212 comprising top and bottom members 214a, 214b and a suture retriever component (or needle shield) 250 that is secured to the jaw mechanism 212 top member 214a. As illustrated in FIGS. 14-16, the jaw mechanism 212 bottom member 214b similarly comprises a guide channel 218b that is configured to receive tubular needle 116 having cleat member 130 disposed in the internal lumen 122 thereof. As further illustrated in FIGS. 14-16, in a preferred embodiment, the guide channel 218b comprises a curvilinear shape or geometry that is configured to approximate the same curvilinear shape or configuration as the formed curvilinear portion 150 of the tubular needle 116.

In a preferred embodiment, guide channel 218b is in aligned communication with the elongated member 104 internal lumen 105.

As illustrated in FIG. 16, the jaw mechanism 112 bottom member 214b comprises a suture loading slot 232 that transects the guide channel 218b of the bottom member 214b.

Figure 17:
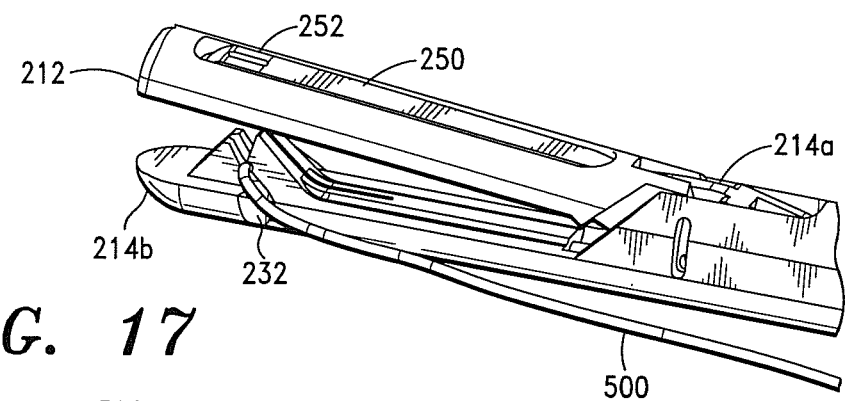
FIG. 17 is a perspective view of the jaw mechanism with the suture laterally loaded in the jaw mechanism bottom member, in accordance with the invention.

As illustrated in FIG. 17, in a preferred embodiment, the suture 500 is loaded via the suture loading slot 232 to enable the suture 500 to slidably translate therethrough and intersect a path defined by the guide channel 218b, where the suture 500 can be engaged by the tubular needle 116 as it is slidably translated through guide channel 218b.

Figure 18:
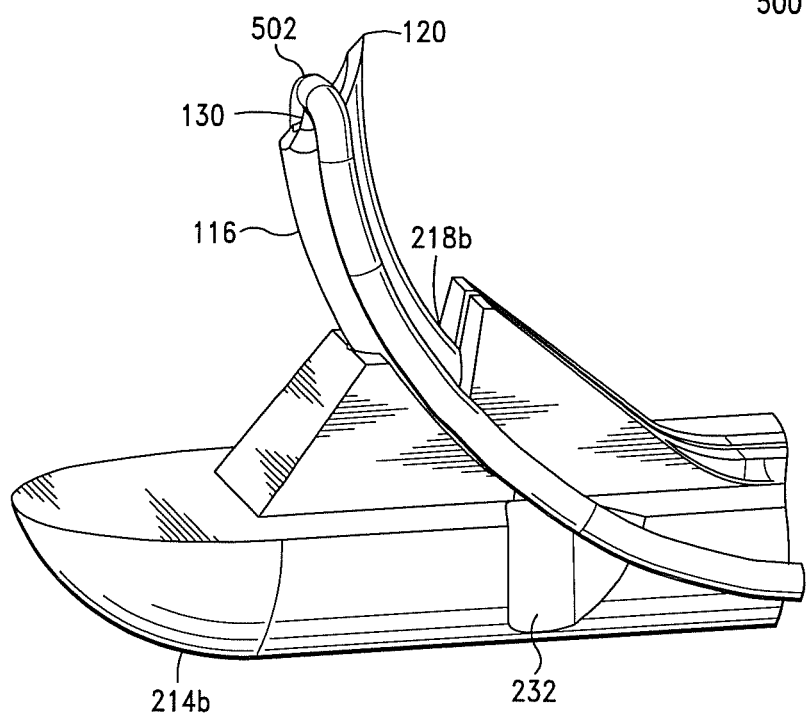
FIG. 18 a perspective view of the elongated member distal tip, jaw mechanism, and tubular needle extended with suture, in accordance with the invention.
Figure 19:
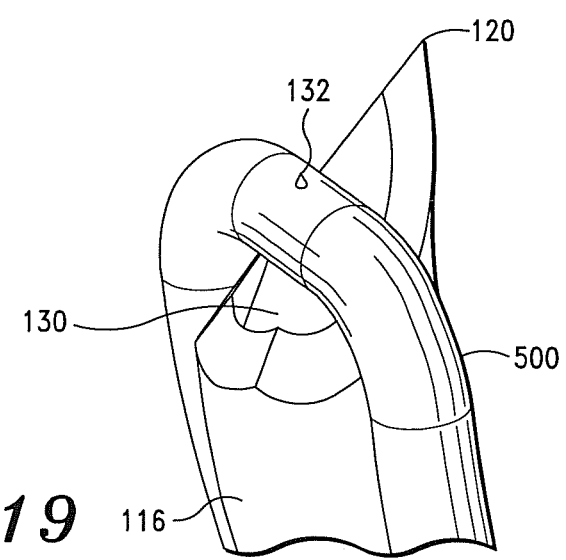
FIG. 19 is a perspective view of the device's tubular needle with cleat member laterally engaged with suture, in accordance with the invention.

As illustrated in FIGS. 18 and 19, in a preferred embodiment, when the tubular needle 116 having cleat member 130 disposed therein is slidably translated through guide channel 218b, the cleat member 130 distal end pierces and engages at least a portion of suture 500. As the tubular needle 116 is slidably translated further through the guide channel 218b of jaw mechanism 212 bottom member 214b, the tubular needle 116 drives the portion of suture 500 forward and into the jaw mechanism 212 top member 214a.

As further illustrated in FIG. 18, in a preferred embodiment, the curvilinear portion 150 of the tubular needle 116 is adapted to transition from a constrained state to an unconstrained state and reassume a curvilinear shape upon further advancement out of guide channel 218b.

Figure 20:
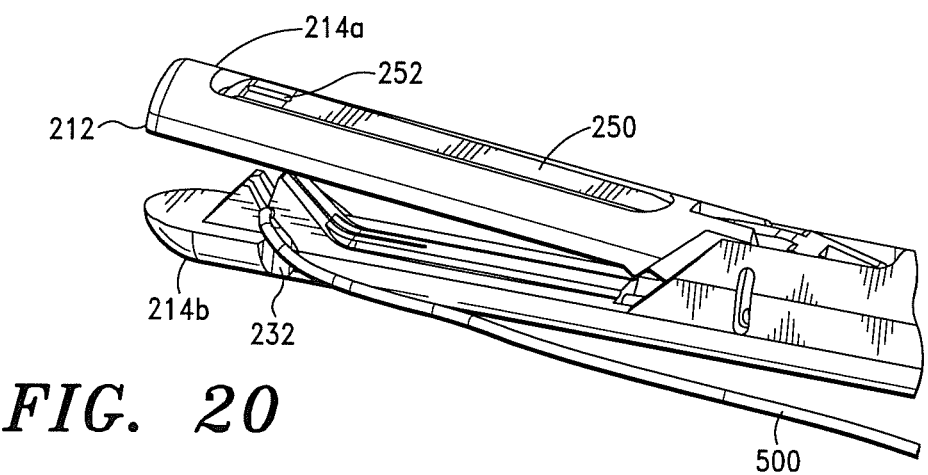
FIG. 20 is a perspective view of the elongated member distal tip and jaw mechanism, with the needle shield in the natural state, in accordance with the invention.
Figure 21:
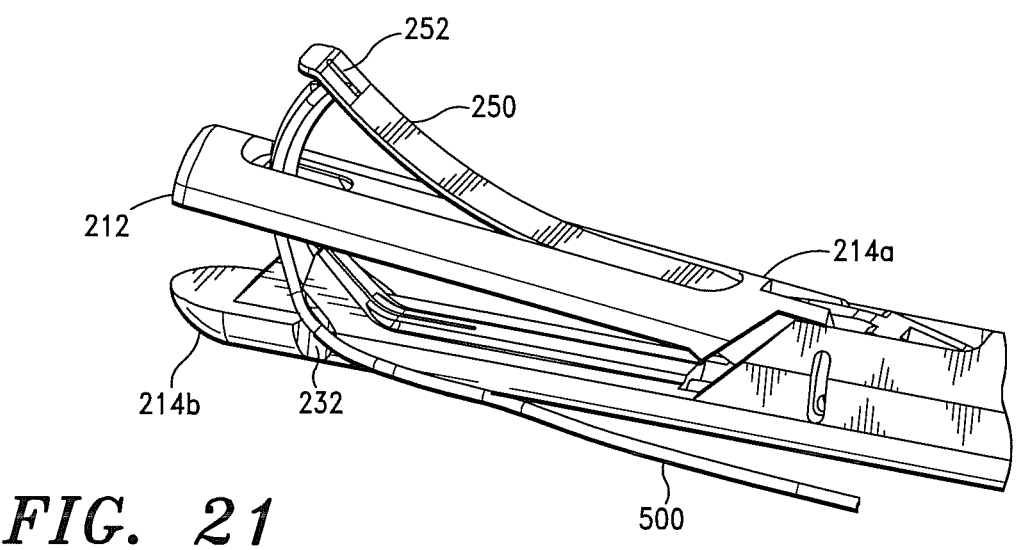
FIG. 21 is a perspective view of the jaw mechanism with the needle shield in the deflected state, shielding the needle distal end from surrounding tissue, in accordance with the invention.
Figure 22:
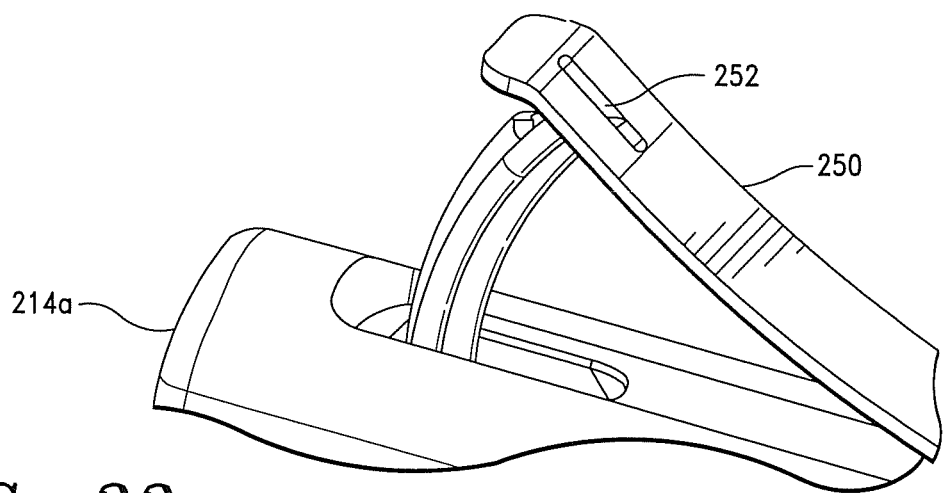
FIG. 22 is a perspective view of the jaw mechanism with the needle shield in the deflected state, showing a window feature in the needle shield to prevent damage to the tubular needle distal end, in accordance with the invention.

Referring now to FIGS. 20-22, when the tubular needle 116 is slidably translated through the guide channel 218b and into the jaw mechanism 212 top member 214a, the tubular needle 116 is guided into needle shield 250. As illustrated in FIG. 20, in a preferred embodiment, the needle shield 250 comprises a deflecting trapdoor mechanism that is configured to prevent the tubular needle 116 from proceeding beyond the top member 214a and damaging local biological tissue and bone. In a preferred embodiment, the needle shield 250 is configured to deflect and flex when the tubular needle 116 distal end 120 is slidably translated into the needle shield 250.

In a preferred embodiment, the needle shield 250 of the jaw mechanism 212 top member 214a enables antegrade and retrograde passing of suture 500 during an endoscopic procedure, which allows an operator to generate a wide variety of stitch patterns including, without limitation, modified Mason-Allen, mattress, sliding mattress, Mason-Allen, far-near-near-far, Bunnell-Mayer, three-loop pulley, locking loop, modified Kessler, simple interrupted, simple continuous, Ford interlocking, interrupted cruciate, interrupted horizontal mattress, continuous horizontal mattress, interrupted vertical mattress, quilled, interrupted or continuous Lembert, interrupted quilt, Cushing, Connel, Parker-Kerr, purse string and modified variants thereof.

In some embodiments, the needle shield 250 is configured to provide a closure force that captures the suture 500 when the tubular needle 116 is retracted and the needle shield 250 is relived from the force applied by slidable translation of the tubular needle 116. In some embodiments, the needle shield 250 is configured to provide a closure or resistance force in the range of 1.0-25 N, more preferably, a closure force in the range of 5.0-10 N.

As illustrated in FIGS. 20-22, in a preferred embodiment, the needle shield 250 comprises a window member 252 that is configured to protect the distal end 120 of tubular needle 116 from damage. According to the invention, the needle shield 250 can comprise other features to protect the distal end 120 of tubular needle 116, such as a coined recess or other geometry that is configured to receive the distal end 120 of tubular needle 116 without damaging the distal end 120.

According to the invention, the needle shield 250 window member 252 can comprise any shape or size suitable to receive the distal end 120 of tubular needle 116 without damaging the distal end 120.

Figure 23A:
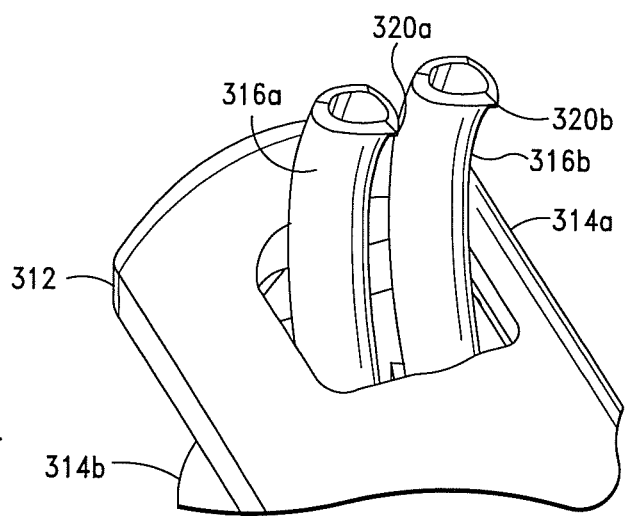
FIG. 23A is a perspective view of two tubular needles extended in another embodiment of the jaw mechanism, in accordance with the invention.
Figure 23B:
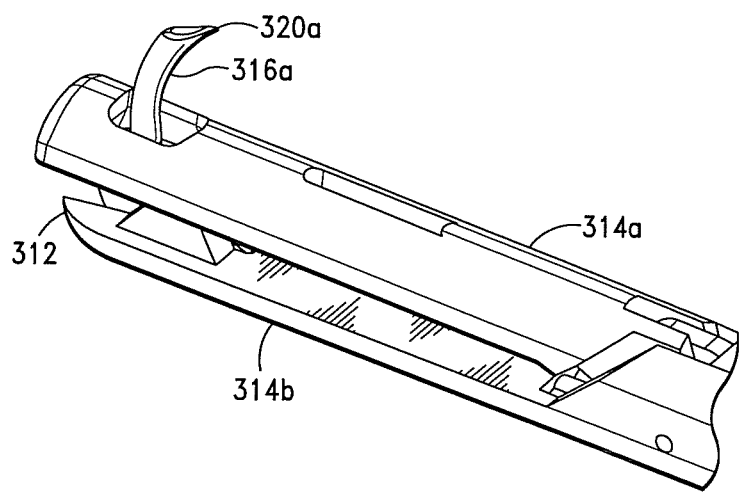
FIG. 23B is a perspective view of the left tubular needle extended in the jaw mechanism, in accordance with the invention.
Figure 23C:
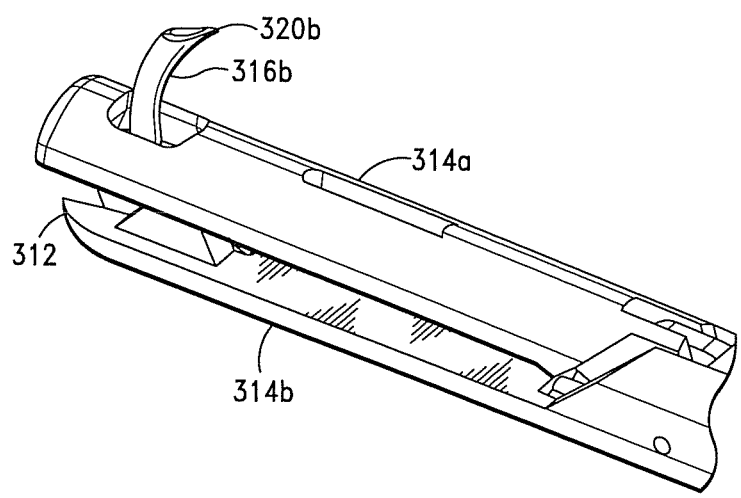
FIG. 23C is a perspective view of the right tubular needle extended in the jaw mechanism, in accordance with the invention.

Referring now to FIGS. 23A-23C, there is shown another embodiment of jaw mechanism 312 comprising top and bottom members 314a, 314b. As illustrated in FIG. 23A, the jaw mechanism 312 bottom member 314b comprises two (2) guide channels (not shown) that are configured to receive first and second tubular needles 316a, 316b.

As illustrated in FIG. 23A, in some embodiments, the suture passing device 100 is configured to drive at least two portions of suture 500 through biological tissue. In some embodiments, the portions of suture 500 being driven by tubular needles 316a, 316b are secured in at least one predetermined location along suture 500 to form a continuous loop of suture 500, thereby, enabling the formation of desired suture stitch patterns.

According to the invention, the stitch patterns can comprise any of the aforementioned stitch patterns.

In some embodiments, the actuator 106 of hand grip 102 is configured to modulate the slidable translation of the first and second tubular needles 316a, 316b through the guide channels of jaw mechanism 312 bottom member 314b independently. In some embodiments, the hand grip 102 comprises an additional actuator that is configured to toggle and engage one of the first and second tubular needles 316a, 316b individually. In some embodiments, suture 500 is loaded onto the first and second distal ends 320a, 320b of first and second tubular needles 316a, 316b, respectively.

As illustrated in FIG. 23B, the jaw mechanism 312 can be configured to grasp a first predetermined region of biological tissue (not shown), slidably translate the first tubular needle 316a having a first portion of suture 500 secured thereto (not shown) into and through the first predetermined region of biological tissue. In some embodiments, when the actuator 106 is partially relieved from a radial force and returns to a pre-engagement state, the first tubular needle 316a is retracted and returns to a constrained state.

As illustrated in FIG. 23C, the jaw mechanism 312 can then be repositioned to grasp a second predetermined region of biological tissue (not shown), slidably translate the second tubular needle 316b having a second portion of suture 500 secured thereto (not shown) into and through the second predetermined region of biological tissue. In some embodiments, when the actuator 106 is fully relieved from a radial force and returns to a pre-engagement state, the second tubular needle 316b is retracted and returns to a constrained state. The jaw mechanism 312 is then removed from the second predetermined region of biological tissue to expose the first and second portions of suture 500.

As will readily be appreciated by one having ordinary skill in the art, the present invention provides numerous advantages compared to prior art systems and methods for passing suture through biological tissue. Among the advantages are the following:

The provision of suture passing systems that can be readily employed to effectively approximate, ligate, fixate and/or close biological tissue;

The provision of suture passing systems that can be readily employed to substantially reduce or eliminate needle deflection or skiving;

The provision of suture passing systems that can be readily employed to endure multiple use cycles with limited impact on suture passing efficacy;

The provision of suture passing systems that can be readily employed to be compatible with a plurality of access cannulas;

The provision of suture passing systems that can be readily employed to enable antegrade and retrograde passing of suture during endoscopic surgical procedures;

The provision of suture passing systems that can be readily employed to enable an operator to generate high tensile strength stitch patterns during an endoscopic procedure, such as a modified Mason-Allen stitch;

The provision of suture passing systems that can be readily employed to pass suture without collateral damage to extraneous soft tissue and bone structures; and The provision of suture passing systems that can be readily employed to pass suture through biological tissue structures having a wide range of thicknesses.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A suture passing device, comprising:
 a suture;
 a hand grip;
 a needle assembly comprising a deformable tubular needle, said deformable tubular needle comprising a tissue piercing first distal end, a first internal lumen and a curvilinear portion, said curvilinear portion of said deformable tubular needle being configured to transition from a plurality of constrained states to an unconstrained state, and from said unconstrained state to said plurality of constrained states, said deformable tubular needle first distal end being configured to releasably engage said suture;
 a cleat member disposed at least partially within said first internal lumen of said deformable tubular needle, said cleat member comprising a second distal end forming a bevel, said cleat member being configured to protrude distally outward from said deformable tubular needle first internal lumen, said cleat member being configured to releasably engage said suture; and
 an elongated tubular member in communication with said hand grip comprising a third distal end, a second internal lumen and a jaw mechanism,
 said second internal lumen being configured to receive said deformable tubular needle and allow said deformable tubular needle to slidably translate therethrough when said deformable tubular needle is in a first constrained state of said plurality of constrained states,
 said jaw mechanism being disposed proximate said tubular member third distal end, said jaw mechanism comprising a first guide channel in aligned communication with said tubular member second internal lumen, said first guide channel comprising a first curvilinear geometry that is configured to approximate and receive said curvilinear portion of said deformable tubular needle when said deformable tubular needle is slidably translated therethrough, whereby said deformable tubular needle transitions from a second constrained state of said plurality of constrained states to said unconstrained state when said deformable tubular needle is slidably translated into and through said first guide channel.

2. The device of claim 1, wherein said deformable tubular needle comprises nickel-titanium alloy.

3. The device of claim 1, wherein said jaw mechanism comprises a top member comprising a top member proximal end and a bottom member comprising a bottom member proximal end.

4. The device of claim 3, wherein said jaw mechanism further comprises first and second pins, said proximal end of said jaw mechanism top member comprises first and second pin lumens, and said proximal end of said jaw mechanism bottom member comprises a third pin lumen and a pin slot, said first pin lumen and said pin slot being in axial alignment, and said second and third pin lumens being in axial alignment.

5. The device of claim 4, wherein said jaw mechanism top member first pin lumen and said bottom member pin slot are configured to receive and position said jaw mechanism first pin, and wherein, when said jaw mechanism first pin is received by and positioned in said jaw mechanism top member first pin lumen and said bottom member pin slot, said jaw mechanism top member is allowed to vertically articulate with respect to said jaw mechanism bottom member.

6. The device of claim 4, wherein said jaw mechanism top member second pin lumen and said bottom member third pin lumen are configured to receive and position said jaw mechanism second pin, and wherein, when said jaw mechanism second pin is received by and positioned in said jaw mechanism top member second pin lumen and said bottom member third pin lumen, said jaw mechanism top member is allowed to axially articulate with respect to said jaw mechanism bottom member.

7. The device of claim 6, wherein said hand grip comprises an actuator in operative communication with said deformable tubular needle and said jaw mechanism top and bottom members.

8. The device of claim 7, wherein said actuator is configured to modulate said axial articulation of said jaw mechanism top member relative to said jaw mechanism bottom member and said slidable translation of said deformable tubular needle.

* * * * *